(12) United States Patent
Hagihara et al.

(10) Patent No.: US 11,932,841 B2
(45) Date of Patent: Mar. 19, 2024

(54) CELL CULTIVATION MODULE

(71) Applicant: UBE CORPORATION, Yamaguchi (JP)

(72) Inventors: Masahiko Hagihara, Yamaguchi (JP); Shinsaku Fuse, Yamaguchi (JP); Motohisa Shimizu, Yamaguchi (JP); Yukinori Wada, Yamaguchi (JP)

(73) Assignee: UBE CORPORATION, Yamaguchi (JP)

(*) Notice: Subject to any disclaimer, the term of this patent is extended or adjusted under 35 U.S.C. 154(b) by 232 days.

(21) Appl. No.: 16/319,794

(22) PCT Filed: Jul. 25, 2017

(86) PCT No.: PCT/JP2017/026948
§ 371 (c)(1),
(2) Date: Jan. 22, 2019

(87) PCT Pub. No.: WO2018/021368
PCT Pub. Date: Feb. 1, 2018

(65) Prior Publication Data
US 2019/0330581 A1  Oct. 31, 2019

(30) Foreign Application Priority Data

Jul. 25, 2016 (JP) ................. 2016-145844

(51) Int. Cl.
*C12M 1/12* (2006.01)
(52) U.S. Cl.
CPC .................. *C12M 25/02* (2013.01)
(58) Field of Classification Search
CPC .......... C12M 25/02; C12N 11/08; C12N 1/20; C12N 5/0068; C12N 1/16; C12N 2533/30; C08L 79/08
See application file for complete search history.

(56) References Cited

U.S. PATENT DOCUMENTS

| | | | | |
|---|---|---|---|---|
| 5,344,454 A | * | 9/1994 | Clarke | A61K 9/0024 623/23.72 |
| 2004/0132175 A1 | * | 7/2004 | Vetillard | C12M 25/16 435/297.1 |

(Continued)

FOREIGN PATENT DOCUMENTS

| CA | 2 969 197 A | 8/2016 |
|---|---|---|
| CA | 2 974 276 A | 8/2016 |

(Continued)

OTHER PUBLICATIONS

European Search Report corresponding to EP 17834370.3 dated Mar. 13, 2020; 12 pages.

(Continued)

*Primary Examiner* — William H. Beisner
*Assistant Examiner* — Danielle B Henkel
(74) *Attorney, Agent, or Firm* — Mintz Levin Cohn Ferris Glovsky and Popeo, P.C.

(57) ABSTRACT

The present invention provides a cell cultivation module comprising a polymer porous film and a casing that has two or more culture medium inflow/outflow ports and accommodates the polymer porous film, wherein the polymer porous film is a polymer porous film with a three-layer structure, having a surface layer A and a surface layer B that have a plurality of holes, and a macrovoid layer that is sandwiched between the surface layer A and the surface layer B, the average hole diameter of the holes present in the surface layer A is smaller than the average hole diameter of the holes present in the surface layer B, the macrovoid layer has dividing walls that are connected to the surface layers A and B, and a plurality of macrovoids that are surrounded by the dividing walls and the surface layers A and B, the holes in the surface layers A and B are in communication with the (Continued)

macrovoids, and the polymer porous film is accommodated within the casing.

11 Claims, 26 Drawing Sheets

(56) References Cited

U.S. PATENT DOCUMENTS

| | | | | |
|---|---|---|---|---|
| 2006/0240544 | A1* | 10/2006 | Shiau | C12M 27/14 |
| | | | | 435/292.1 |
| 2011/0318556 | A1 | 12/2011 | Ohya et al. | |
| 2012/0156773 | A1* | 6/2012 | Smith | C12N 5/0068 |
| | | | | 435/395 |
| 2014/0038279 | A1* | 2/2014 | Ingber | C12M 23/38 |
| | | | | 435/297.2 |
| 2016/0168560 | A1 | 6/2016 | Hagihara et al. | |
| 2018/0042220 | A1* | 2/2018 | Miyagawa | A01N 1/021 |

FOREIGN PATENT DOCUMENTS

| | | |
|---|---|---|
| CA | 3 031 921 A | 2/2018 |
| EP | 0 402 272 S2 | 12/1990 |
| EP | 2 354 180 A1 | 8/2011 |
| EP | 3 026 108 A1 | 6/2016 |
| EP | 3 489 351 A1 | 5/2019 |
| JP | 63-196286 A | 8/1988 |
| JP | 63-198975 A | 8/1988 |
| JP | 63-1918978 A | 8/1988 |
| JP | H03-10674 A | 1/1991 |
| JP | 2011-219585 A | 11/2011 |
| JP | 2011-219586 A | 11/2011 |
| WO | 03/054174 A1 | 7/2003 |
| WO | 2010/038873 A1 | 4/2010 |
| WO | 2015/012415 A1 | 1/2015 |

OTHER PUBLICATIONS

Maenosono, Hirotaka et al., "A Transparent Polyimide Film as a Biological Cell Culture Sheet with Microstructures," *Journal of Biomaterials and Nanobiotechnology* (2014; accepted Dec. 28, 2013); 5:17-23. See English Abstract.

Database WPI Week 198838; *Thomson Scientific, London, GB*; AN 1988-268203 XP002798043 & JP S63 196286A (Sumitomo Electric Ind Co) Aug. 15, 1988 (Aug. 15, 1988) *abstract* [Also, see JP 63-196286 submitted in IDS dated Mar. 22, 2019; Cite No. 4 with English language Abstract].

International Search Report dated Oct. 24, 2017 corresponding to International Patent Application No. PCT/JP2017/026948, filed on Jul. 25, 2017, 2 pages.

* cited by examiner

FIG. 4
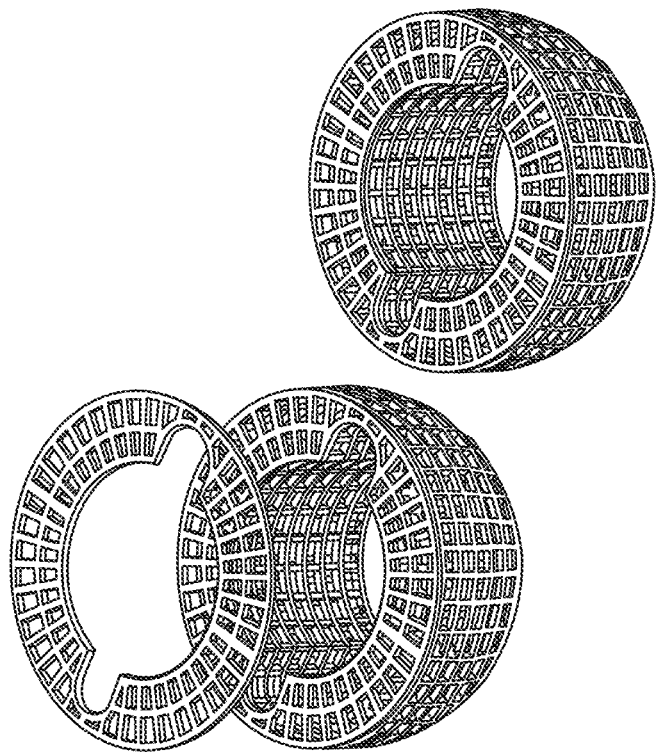
(B)
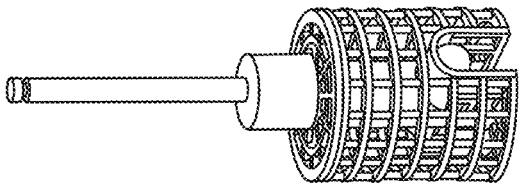
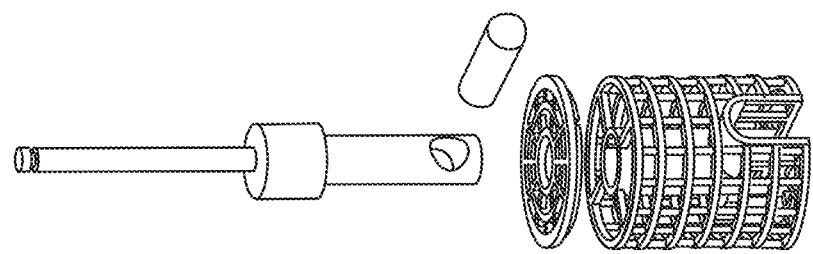
(A)

FIG. 5
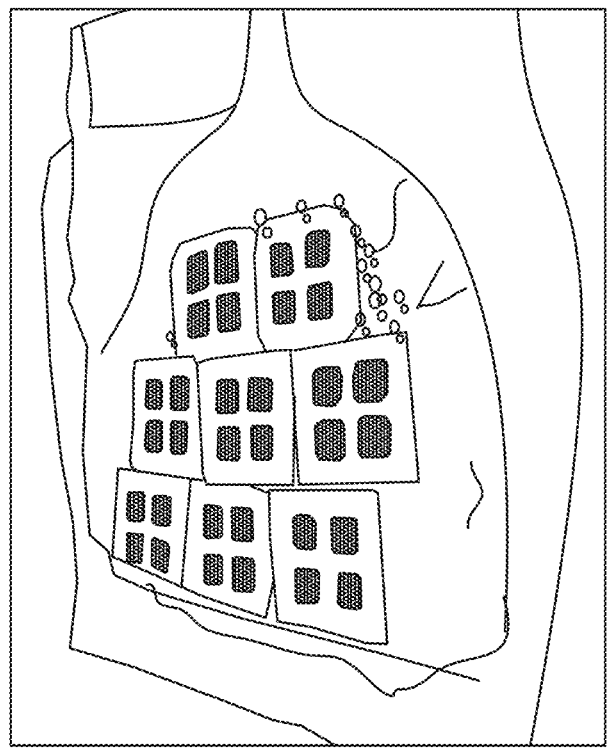
ONE HOUR AFTER MEDIUM EXCHANGE
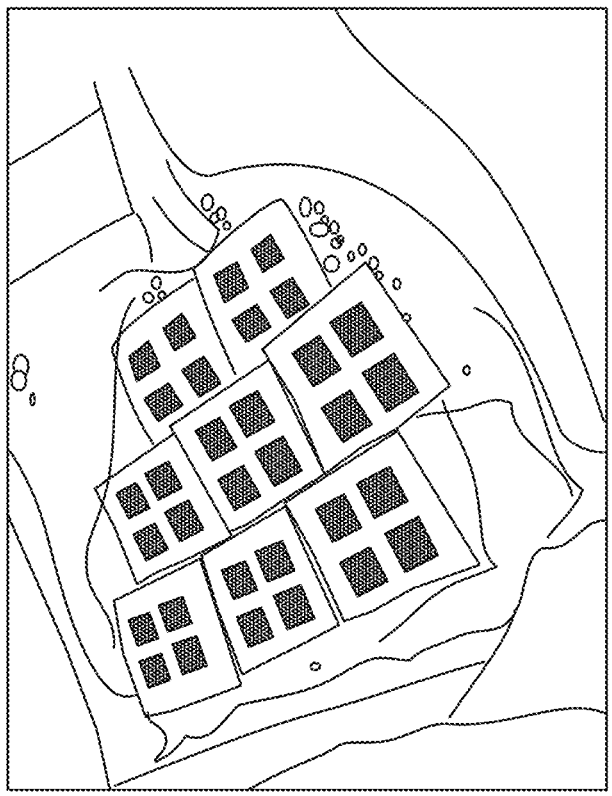
AT THE TIME OF MEDIUM EXCHANGE FIG. 10
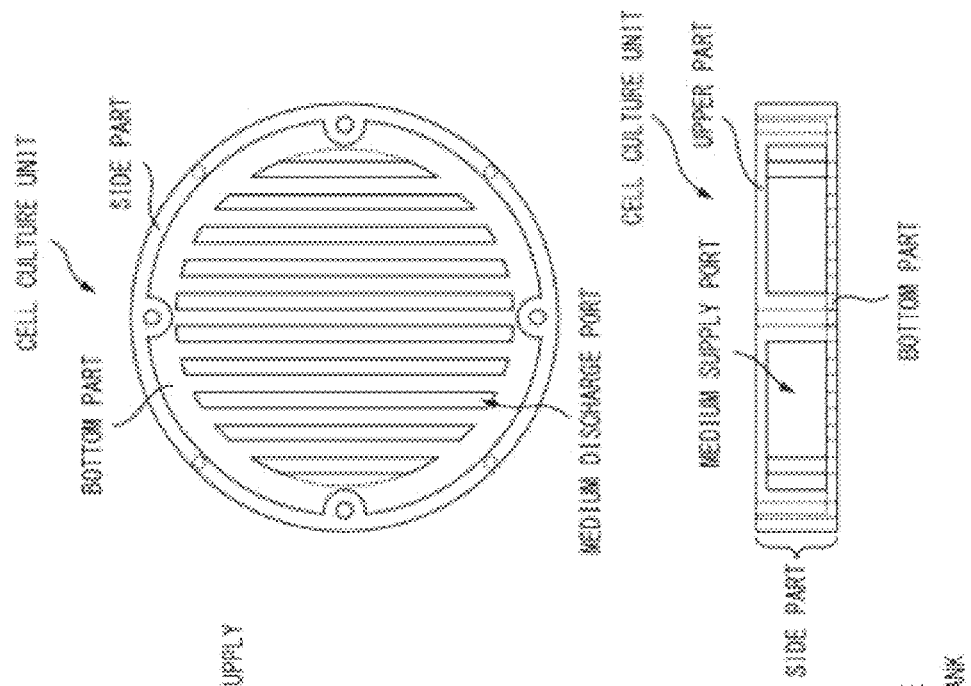
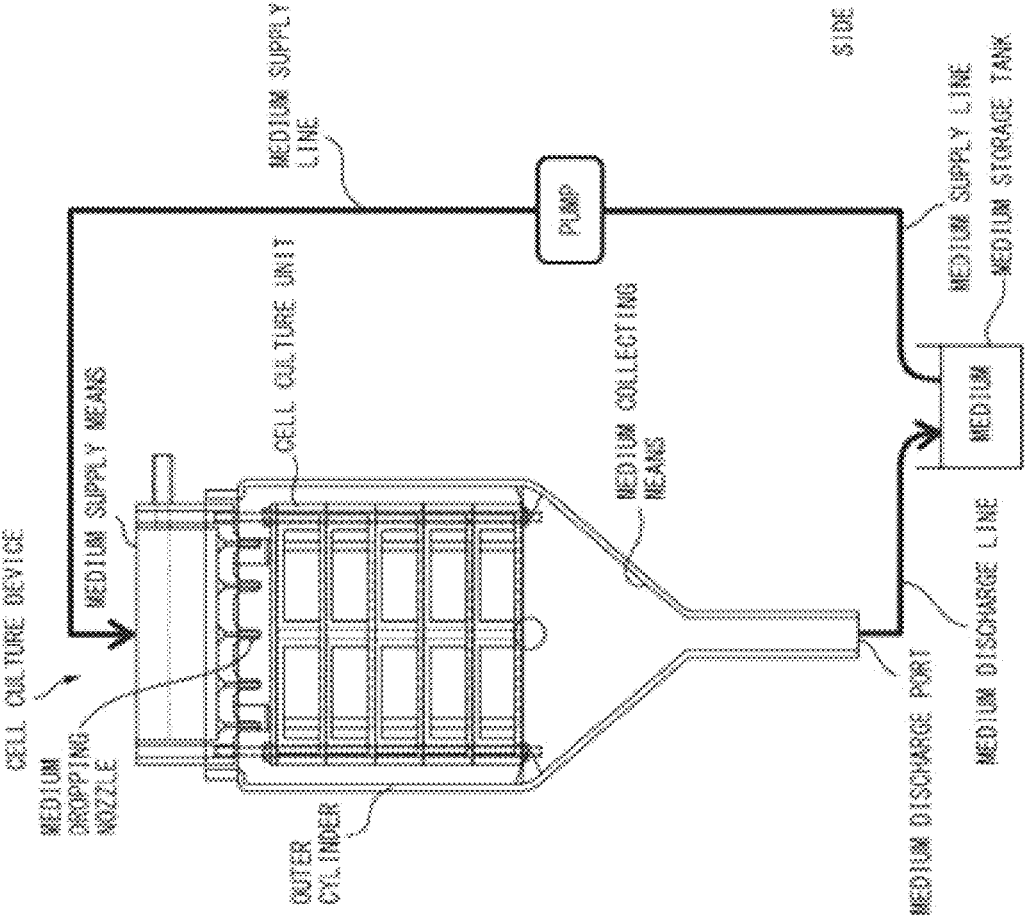

FIG. 15

| EXPERIMENT NAME | SHAPE OF POROUS POLYIMIDE FILM | PHOTOGRAPH OF MODULE | SHAPE OF MODULE |
|---|---|---|---|
| 1 | 7mm × 7mm 8 PIECES | | PLANAR TYPE |
| 2 | 7mm × 7mm 8 PIECES | | PARTIALLY PENETRATING TYPE |
| 3 | 3.5mm × 3.5mm 16 PIECES | | PLANAR TYPE |
| 4 | 3.5mm × 3.5mm 16 PIECES | | PARTIALLY PENETRATING TYPE |
| 5 | 14mm × 5mm 6 PIECES | | 2-POINT FIXED/EXPOSED TYPE |
| 6 | 7mm × 7mm 8 PIECES | | 1-POINT FIXED/EXPOSED TYPE |

FIG. 18
(A)
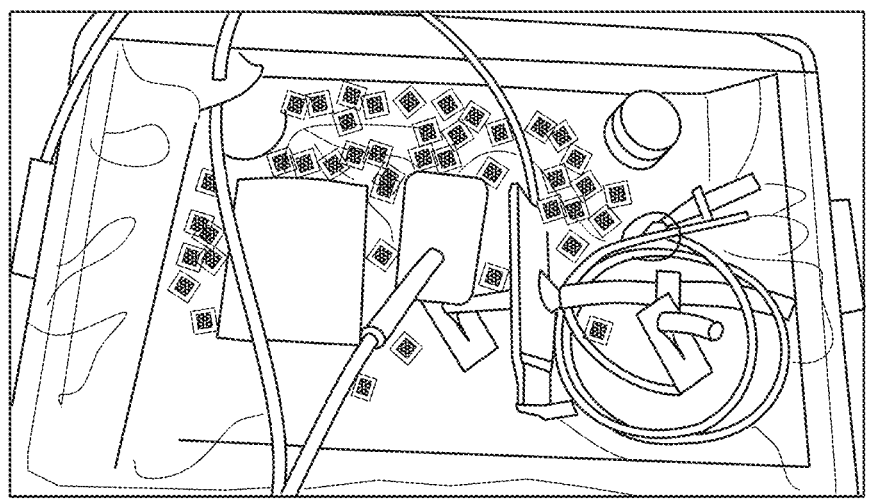
(B)
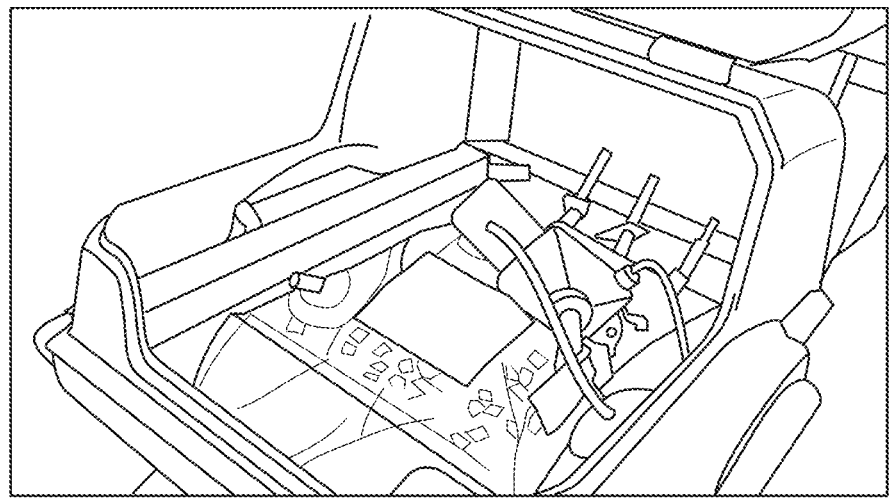

FIG. 20
(A)
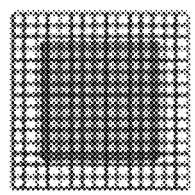
(B)
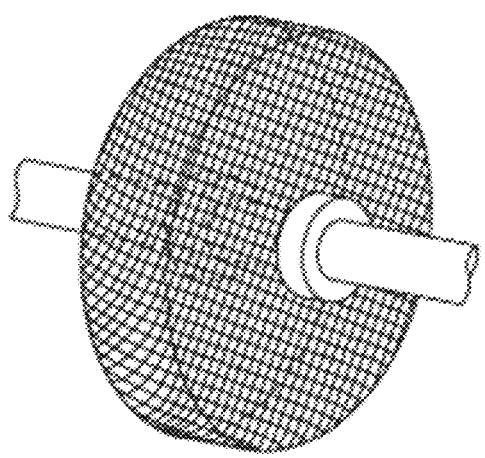
(C)
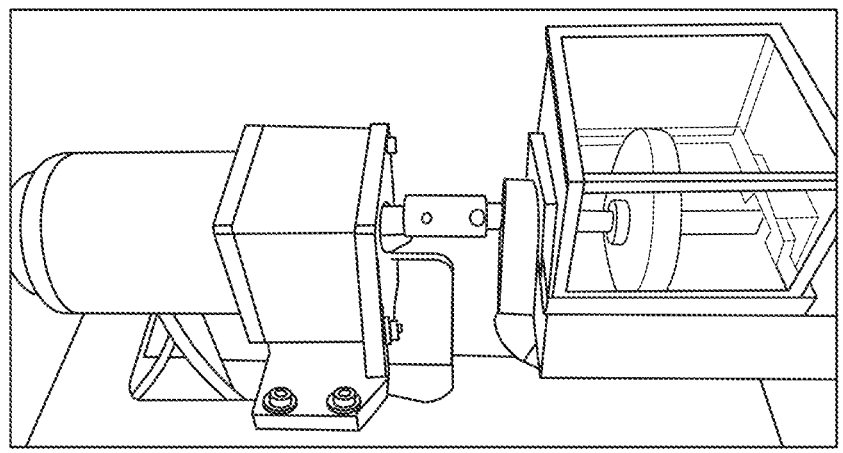

CELL CULTIVATION MODULE

FIELD

The present invention relates to a cell culture module.

BACKGROUND

In recent years, proteins such as enzymes, hormones, antibodies, cytokines, viruses (viral proteins) used for treatment and vaccine are industrially produced using cultured cells. However, such a protein production technology is expensive, raising medical cost. Accordingly, there have been demands for innovating technologies for culturing cells at high density and for increasing protein production, aiming at great reduction of cost.

As cells for protein production, anchorage-dependent adherent cells which adhere to a culture substrate may be sometimes used. Since such cells grow anchorage-dependently, they need to be cultured while being adhered onto the surface of a dish, plate or chamber. Conventionally, in order to culture such adherent cells in a large amount, it was preferable to increase the surface area to be adhered. However, increasing the culturing area inevitably requires to increase the space, which is responsible for increase in cost.

As a method to culture a large amount of adherent cells while decreasing the culture space, a method for culture using a microporous carrier, especially a microcarrier, has been developed (for example, PTL 1). In a cell culturing system using microcarriers, it is preferable to carry out sufficient stirring and diffusion so that the microcarriers do not aggregate together. Since this requires a volume allowing adequate agitation and diffusion of the medium in which the microcarriers are dispersed, there is an upper limit to the density at which the cells can be cultured. In order to separate the microcarrier from the medium, separation is preferably performed using a filter which can separate fine particles, possibly resulting in increased cost. Considering the foregoing, there is a demand for innovative methodology for cell culture which cultures cells at high density.

<Porous Polyimide Film>

Porous polyimide films have been utilized in the prior art for filters and low permittivity films, and especially for battery-related purposes, such as fuel cell electrolyte membrane and the like. PTLs 2 to 4 describe porous polyimide films with numerous macrovoids, having excellent permeability to objects such as gases, high porosity, excellent smoothness on both surfaces, relatively high strength and, despite high porosity, excellent resistance against compression stress in the film thickness direction. All of these are porous polyimide films formed via amic acid.

The cell culture method which includes applying cells to a porous polyimide film and culturing them is reported (PTL 5).

CITATION LIST

Patent Literature

[PTL 1] WO2003/054174
[PTL 2] WO2010/038873
[PTL 3] Japanese Unexamined Patent Publication (Kokai) No. 2011-219585
[PTL 4] Japanese Unexamined Patent Publication (Kokai) No. 2011-219586
[PTL 5] WO2015/012415

SUMMARY

Technical Problem

It is an object of the present invention to provide a method for cell culture. It is another object of the invention to provide a method for removing a cell from a cell suspension. It is still another object of the invention to provide a method for killing a cell in a cell suspension. Further, it is another object of the present invention to provide a cell culture module.

Solution to Problem

The present inventors have found that the porous polymer film having a prescribed structure is suitable for mass cell culture and removal of cells. The present inventors have also found that the porous polymer film having a prescribed structure is suitable for killing cells under prescribed conditions. In other words, the present invention preferably includes, but is not limited to, the following modes.

[1] A method for culturing a cell, the method comprising the steps of:

(1) applying a cell culture module to a first medium containing a cell;

(2) maintaining a temperature at which the cell can be cultured, and adsorbing the cell to the cell culture module, and (3) culturing the cell culture module having the cell adsorbed, in a second medium in a culture vessel;

wherein the cell culture module comprising:

a porous polymer film; and a casing having two or more medium flow inlets, the casing containing the porous polymer film, wherein the porous polymer film is a three-layer structure porous polymer film having a surface layer A and a surface layer B, the surface layers having a plurality of pores, and a macrovoid layer sandwiched between the surface layers A and B;

wherein an average pore diameter of the pores present in the surface layer A is smaller than an average pore diameter of the pores present in the surface layer B;

wherein the macrovoid layer has a partition wall bonded to the surface layers A and B, and a plurality of macrovoids surrounded by such a partition wall and the surface layers A and B;

wherein the pores in the surface layers A and B communicate with the macrovoid; and wherein in the casing, (i) the two or more independent porous polymer films being aggregated;

(ii) the porous polymer films being folded up;

(iii) the porous polymer films being wound into a roll-like shape; and/or (iv) the porous polymer films being contained, being tied together into a rope-like shape;

wherein no surfactant is contained in the second medium.

[2] The method according to [1], wherein the diameter of the medium flow inlet is larger than the diameter of the cell, and smaller than the diameter at which the porous polymer films flow out.

[3] The method according to [1] or [2], wherein the casing has a mesh-like structure.

[4] The method according to any one of [1] to [3], wherein the casing consists of an inflexible material.

[5] The method according to any one of [1] to [4], wherein the step (2) is a step, wherein the cell is adsorbed to the porous polymer film while standing, shaking and/or stirring.

[6] The method according to any one of [1] to [5], wherein the step (3) is carried out in a system in which the cell culture medium is continuously or intermittently supplied into the culture vessel.

[7] The method according to any one of [1] to [6], wherein in the culture in the step (3), a part of the porous polymer film is not in contact with the liquid phase of a cell culture medium.

[8] The method according to any one of [1] to [7], wherein in the culture in the step (3), the culture vessel is a flexible bag type culture vessel.

[9] The method according to any one of [1] to [7], wherein in the culture in the step (3), the culture vessel is an agitating culture vessel.

[10] The method according to any one of [1] to [9], wherein the porous polymer film has a plurality of pores having an average pore diameter of 0.01 to 100 μm.

[11] The method according to any one of [1] to [10], wherein an average pore diameter of the surface layer A is 0.01 to 50 μm.

[12] The method according to any one of [1] to [11], wherein an average pore diameter of the surface layer B is 20 to 100 μm.

[13] The method according to any one of [1] to [12], wherein a total film thickness of the porous polymer film is 5 to 500 μm.

[14] The method according to any one of [1] to [13], wherein the porous polymer film is a porous polyimide film.

[15] The method according to [14], wherein the porous polyimide film is a porous polyimide film comprising a polyimide derived from tetracarboxylic dianhydride and diamine.

[16] The method according to [14] or [15], wherein the porous polyimide film is a colored porous polyimide film that is obtained by molding a polyamic acid solution composition comprising a polyamic acid solution derived from tetracarboxylic dianhydride and diamine, and a coloring precursor, and subsequently heat-treating the resultant composition at 250° C. or higher.

[17] The method according to any one of [1] to [13], wherein the porous polymer film is a porous polyethersulfone film.

[18] The method according to any one of [1] to [17], wherein the cell is an adherent cell.

[19] The method according to any one of [1] to [18], wherein the cell is selected from the group consisting of CHO cells, Vero cells, MDCK cells, and fibroblasts.

[20] A method for removing a cell from a cell suspension, the method comprising the steps of:

(1) applying a porous polymer film to a medium containing the cell; and (2) maintaining a temperature at which the cell can be cultured and allowing the cell to be adsorbed onto the porous polymer film;

wherein the porous polymer film is a three-layer structure porous polymer film having a surface layer A and a surface layer B, the surface layers having a plurality of pores, and a macrovoid layer sandwiched between the surface layers A and B;

wherein an average pore diameter of the pores present in the surface layer A is smaller than an average pore diameter of the pores present in the surface layer B;

wherein the macrovoid layer has a partition wall bonded to the surface layers A and B, and a plurality of macrovoids surrounded by such a partition wall and the surface layers A and B.

[21] A method for killing a cell in a cell suspension, the method comprising the steps of:

(1) applying a porous polymer film to a first medium containing the cell;

(2) maintaining a temperature at which the cell can be cultured, and allowing the cell to be adsorbed onto the porous polymer film; and (3) allowing the porous polymer film having the cell adsorbed therein to be floated in a second medium in a culture vessel to culture the porous polymer film by continuously changing the morphology thereof;

wherein the porous polymer film is a three-layer structure porous polymer film having a surface layer A and a surface layer B, the surface layers having a plurality of pores, and a macrovoid layer sandwiched between the surface layers A and B;

wherein an average pore diameter of the pores present in the surface layer A is smaller than an average pore diameter of the pores present in the surface layer B;

wherein the macrovoid layer has a partition wall bonded to the surface layers A and B, and a plurality of macrovoids surrounded by such a partition wall and the surface layers A and B;

wherein the pores in the surface layers A and B communicate with the macrovoid; and wherein no surfactant is contained in the second medium.

[22] A cell culture module comprising:

a porous polymer film; and a casing having two or more medium flow inlets, the casing containing the porous polymer films, wherein the porous polymer films are a three-layer structure porous polymer film having a surface layer A and a surface layer B, the surface layers having a plurality of pores, and a macrovoid layer sandwiched between the surface layers A and B;

wherein an average pore diameter of the pores present in the surface layer A is smaller than an average pore diameter of the pores present in the surface layer B;

wherein the macrovoid layer has a partition wall bonded to the surface layers A and B, and a plurality of macrovoids surrounded by such a partition wall and the surface layers A and B;

wherein the pores in the surface layers A and B communicate with the macrovoid; and wherein the porous polymer film is contained within the casing with:

(i) the two or more independent porous polymer films being aggregated;

(ii) the porous polymer film being folded up;

(iii) the porous polymer film being wound into a roll-like shape; and/or (iv) the porous polymer film being tied together into a rope-like shape.

[23] The cell culture module according to [22], wherein a diameter of the medium flow inlet is larger than a diameter of a cell, and smaller than a diameter at which the porous polymer films flow out.

[24] The cell culture module according to [22] or [23], wherein the casing has a mesh-like structure.

[25] The cell culture module according to any one of [22] to [24], wherein the casing consists of an inflexible material.

[26] The cell culture module according to any one of [22] to [25], wherein the porous polymer film has a plurality of pores having an average pore diameter of 0.01 to 100 µm.

[27] The cell culture module according to any one of [22] to [26], wherein an average pore diameter of the surface layer A is 0.01 to 50 µm.

[28] The cell culture module according to any one of [22] to [27], wherein an average pore diameter of the surface layer B is 20 to 100 µm.

[29] The cell culture module according to any one of [22] to [28], wherein a total film thickness of the porous polymer film is 5 to 500 µm.

[30] The cell culture module according to any one of [22] to [29], wherein the porous polymer film is a porous polyimide film.

[31] The cell culture module according to [30], wherein the porous polyimide film is a porous polyimide film comprising a polyimide derived from tetracarboxylic dianhydride and diamine.

[32] The cell culture module according to [30] or [31], wherein the porous polyimide film is a colored porous polyimide film that is obtained by molding a polyamic acid solution composition comprising a polyamic acid solution derived from tetracarboxylic dianhydride and diamine, and a coloring precursor, and subsequently heat-treating the resultant composition at 250° C. or higher.

[33] The cell culture module according to any one of [22] to [29], wherein the porous polymer film is a porous polyethersulfone film.

Advantageous Effects of Invention

According to the present invention, the suspended cells can be efficiently adsorbed, and can be stably cultured using a conventional suspension culture vessel. In addition, the present invention enables convenient removal of cells without using a filter membrane like in the prior art. Further, when the cells are adsorbed using the porous polymer film according to the present invention, subsequently cultured with continuous morphological deformation, it is possible to conveniently kill the cells and to obtain culture medium in which a protein expressed in the cell is liberated. Further, the porous polymer film which is contained in the casing and modularized is used, enabling convenient adsorption of the cell in the cell suspension as well as convenient and stable cell culture.

BRIEF DESCRIPTION OF DRAWINGS

FIG. 4 represents an embodiment of a device used in combination when the cell culture module is applied in a spinner flask. (A) A rotating type device. The rotating type device to which the cell culture module is applied is placed in a spinner flask and used while rotating the device by itself (B) Stationary type device. The device to which the cell culture module is applied is placed in a bottom part of a spinner flask. The device is used while a stirrer in a spinner flask is rotated in a central space of the device.

FIG. 5 represents an embodiment wherein culture is carried out applying a cell culture module to a flexible bag type vessel. Phenol red in a culture solution turned yellow in 1 hour, the left panel illustrating the culture solution at the beginning of the culture and the right panel illustrating the culture solution 1 hour after beginning of the culture.

FIG. 10 represents an embodiment of a cell culture device used in Example 4. (A) is a diagram illustrating a construction of a cell culture device. (B) is a diagram illustrating a cell culture unit on which a cell culture device is mounted in (A).

FIG. 15 represents several embodiments of a cell culture module used in Example 11.

FIG. 18 represents a diagram illustrating a WAVE-type bioreactor to which a cell culture module according to an embodiment of the present invention is applied. (A) represents a bag enclosing a cell culture module, and (B) represents a step of cell adsorption to the cell culture module using WAVE 25.

FIG. 20 represents a diagram illustrating a cell culture device according to an embodiment of the present invention. (A) represents a cell culture module, (B) represents a cell culture unit, and (C) represents a cell culture device in an embodiment.

DESCRIPTION OF EMBODIMENTS

1. Cell Culture Module

Figure 1:
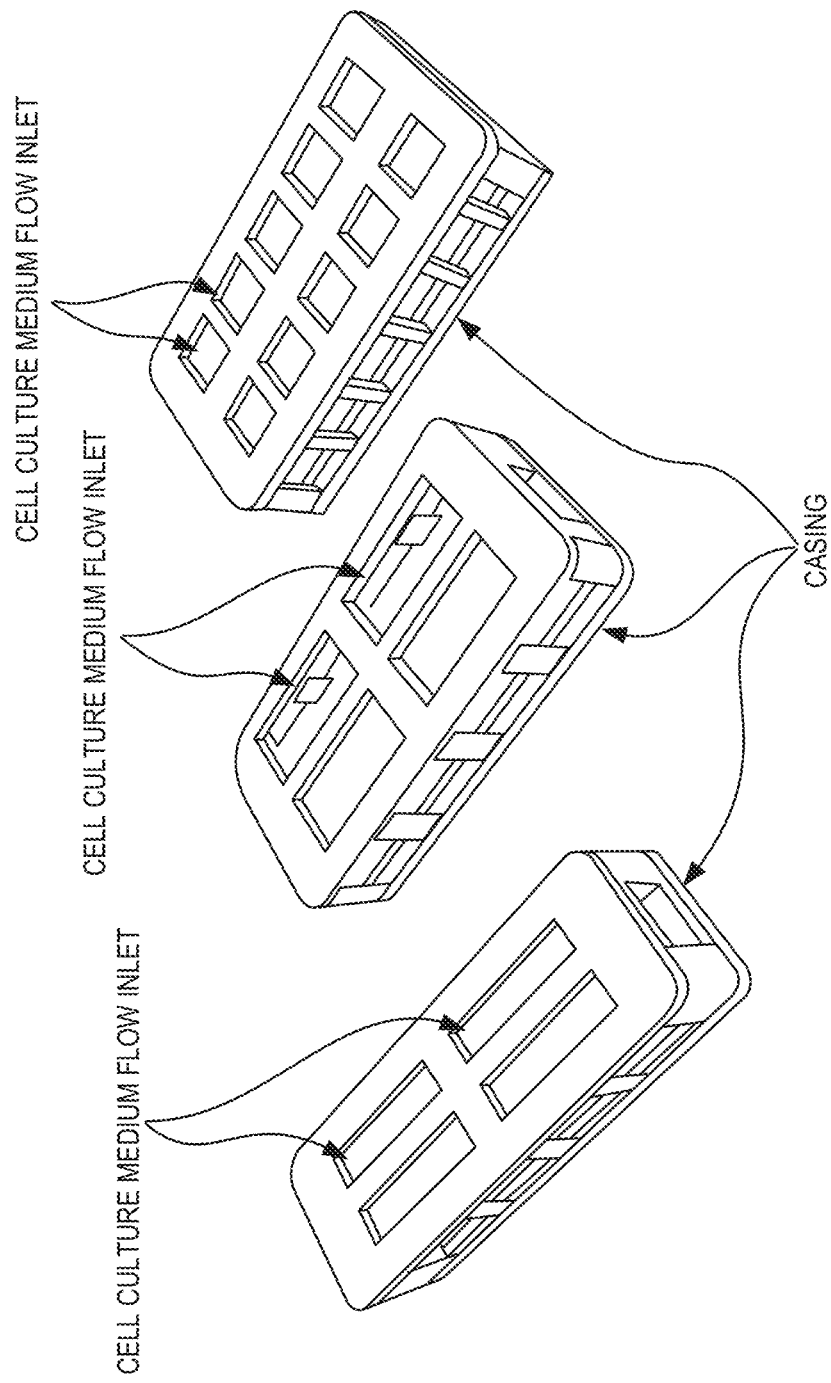
FIG. 1 represents an embodiment of a cell culture module. A porous polymer film is contained in a casing.
Figure 2:
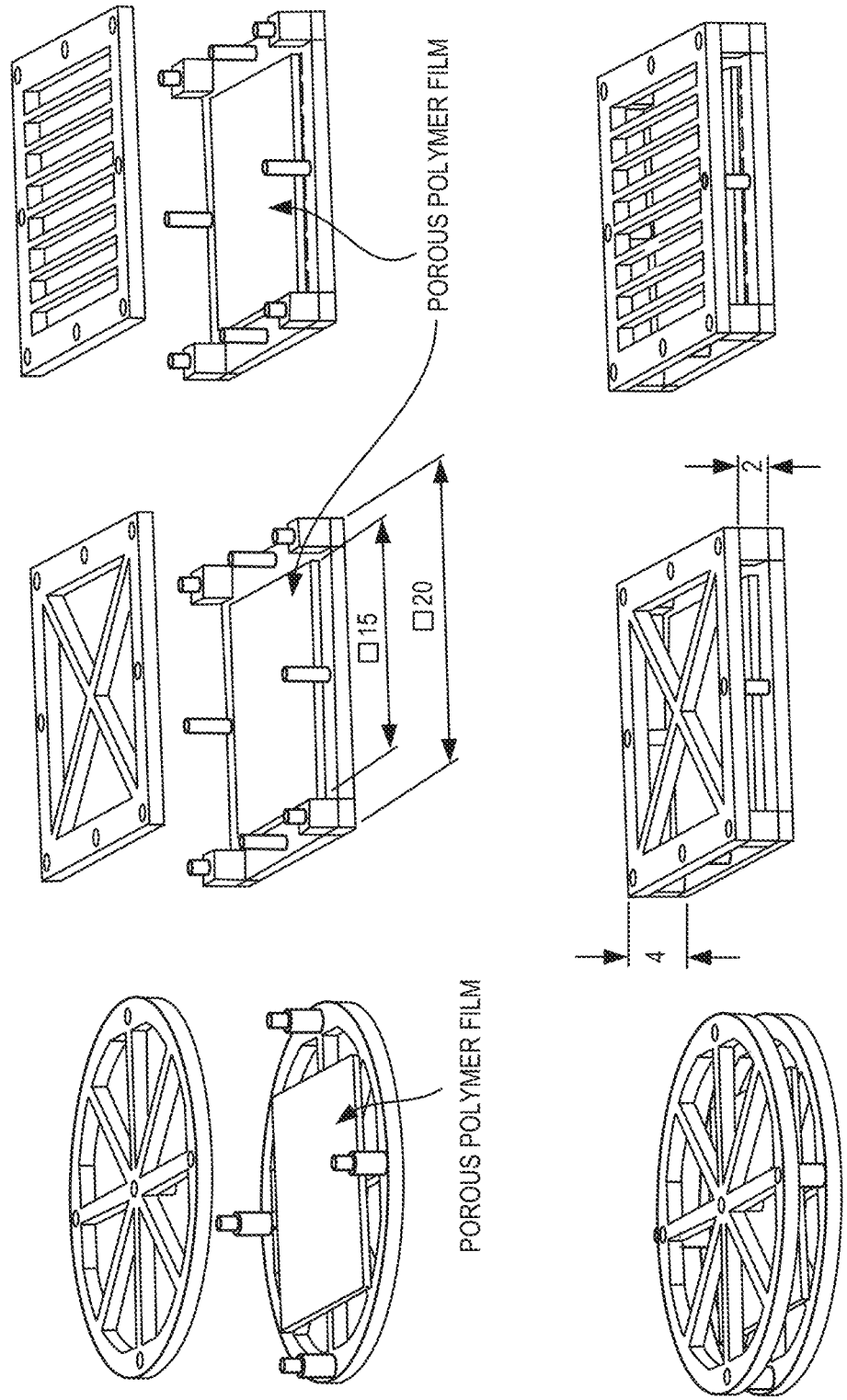
FIG. 2 represents an embodiment of a cell culture module. A porous polymer film is contained in a casing.
Figure 3:
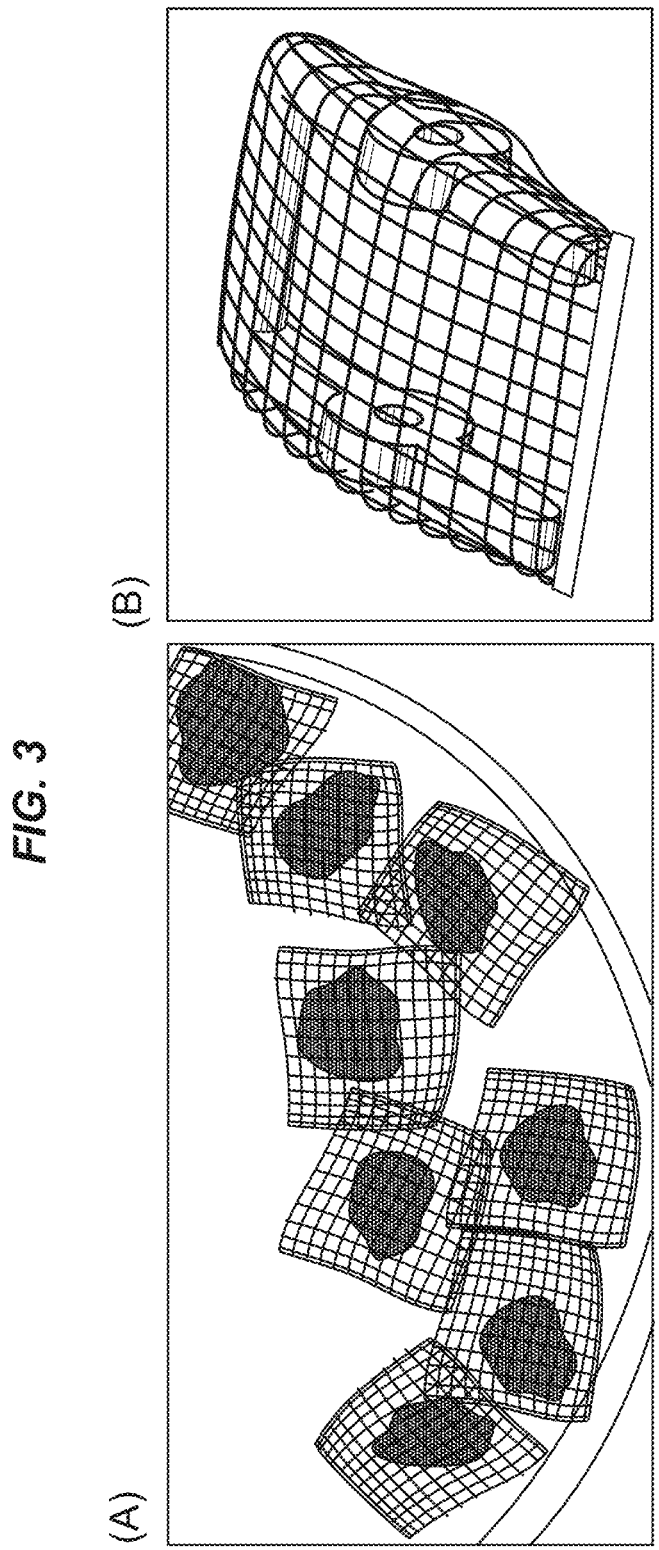
FIG. 3 represents an embodiment of a cell culture module. (A) A porous polymer film is contained in a mesh-like casing. (B) represents an embodiment of a casing composed of a mesh-like net, and a framework.
Figure 6:
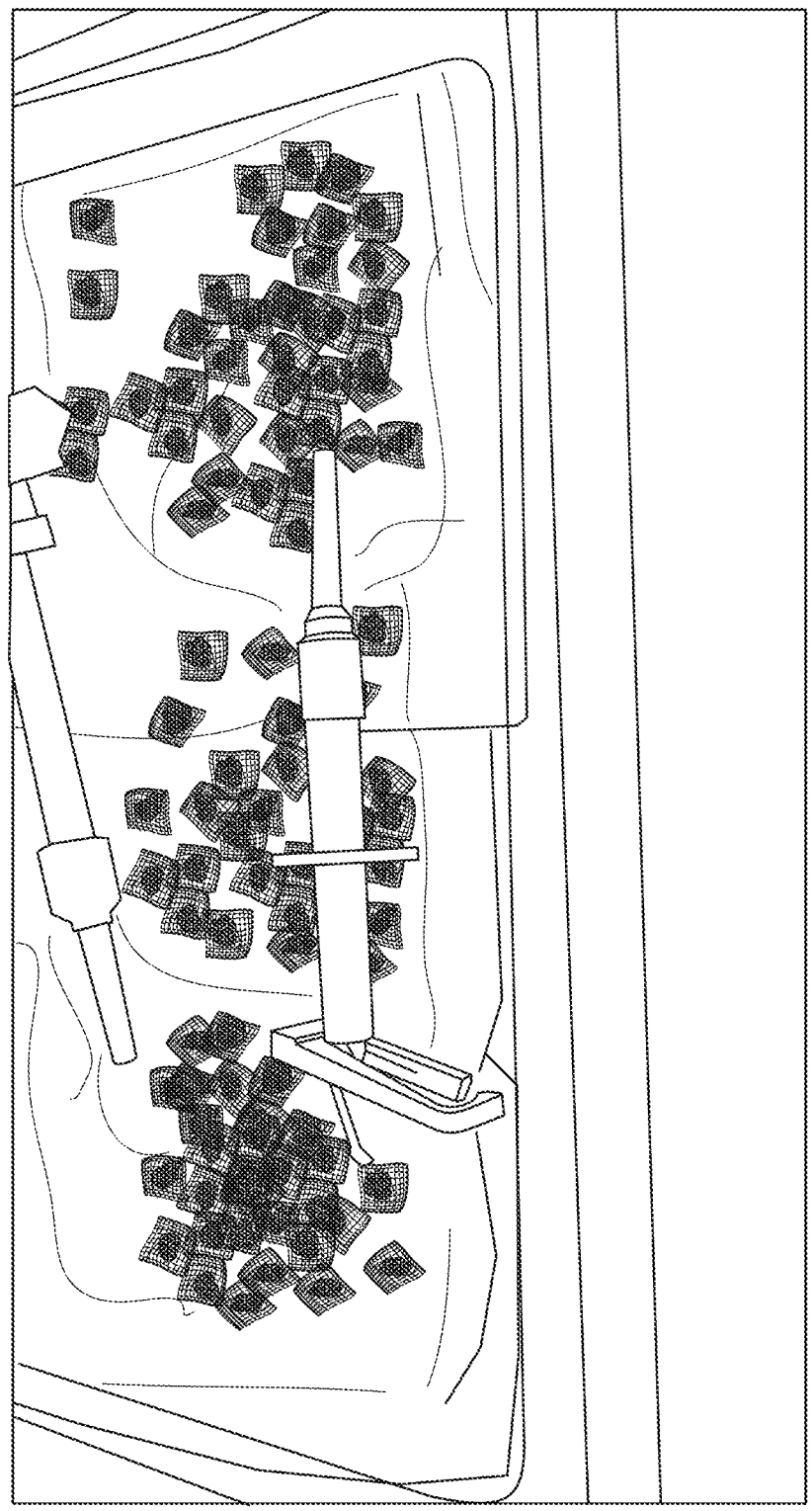
FIG. 6 represents an embodiment of using a mesh-type module during shaking culture.

An embodiment of the invention relates to a cell culture module including:
a porous polymer film; and
a casing having two or more medium flow inlets, the casing containing the porous polymer films,
wherein the porous polymer films are a three-layer structure porous polymer film having a surface layer A and a surface layer B, the surface layers having a plurality of pores, and a macrovoid layer sandwiched between the surface layers A and B;
wherein an average pore diameter of the pores present in the surface layer A is smaller than an average pore diameter of the pores present in the surface layer B;
wherein the macrovoid layer has a partition wall bonded to the surface layers A and B, and a plurality of macrovoids surrounded by such a partition wall and the surface layers A and B;
wherein the pores in the surface layers A and B communicate with the macrovoid; and
wherein the porous polymer film is contained within the casing with:
(i) the two or more independent porous polymer films being aggregated;
(ii) the porous polymer film being folded up;
(iii) the porous polymer film being wound into a roll-like shape; and/or
(iv) the porous polymer film being tied together into a rope-like shape. The cell culture module will be hereinafter referred to as a "cell culture module of the invention". The phrase "a cell culture module" may be expressed simply as "a module", both expression can be used interchangeably to indicate the same meaning.

In this specification, the term "a cell culture module" refers to a cell culture substrate applicable to a cell culture vessel, cell culture device, and cell culture system, especially to a cell culture vessel, cell culture device and cell culture system which can be used for suspension culture. Several embodiments of a cell culture module are depicted in FIGS. 1 to 3, 8, and 20(A). The cell culture module of the invention may be used according to the embodiments such as in FIGS. 4 to 6, 9 to 14, 17, 18, 20, 21 and 24. The cell culture module of the invention may also be used in the embodiments illustrated in Examples described below.

The cell culture module of the invention can prevent continuing morphological deformation of the membrane-like porous polymer film within a casing because of a porous polymer film being contained in the casing. This can protect cells to be grown in the porous polymer film from stress to be applied, resulting in suppression of apoptosis or the like, enabling a stable cell culture in a large amount.

A casing comprised in the cell culture module of the invention has two or more medium flow inlets, which let the cell culture medium be supplied into/discharge from the casing. The diameter of the medium flow inlet of the casing is preferably larger than the diameter of the cell so as to enable cell to flow into the casing. In addition, the diameter of the medium flow inlet is preferably smaller than the diameter through which the porous polymer film flows out from the medium flow inlet. The diameter smaller than the diameter through which the porous polymer film flows out may be appropriately selected depending on the shape and size of the porous polymer film contained in the casing. For example, when the porous polymer film has string-like shape, the diameter is not particularly limited so long as it is smaller than the width of the shorter side of the porous polymer film so that the porous polymer film is prevented from flowing out. It is preferred to provide as many medium flow inlets as possible so that the cell culture medium may be easily supplied into and/or discharged from the casing. It is preferably 5 or more, preferably 10 or more, preferably 20 or more, preferably 50 or more, and preferably 100 or more. As for the medium flow inlet, the casing may have a mesh-like structure in part or as a whole. Moreover, the casing itself may be mesh-like. In the present invention, examples of mesh-like structure include, but not limited to, those including longitudinal, transverse, and/or oblique elements wherein individual apertures form medium flow inlets which allow the fluid to pass therethrough.

It is preferred that the casing contained in the cell culture module of the invention has enough strength not to be deformed by movement of the culture medium under agitation culture, shaking culture conditions, and that casing is formed of a non-flexible material. Moreover, it is preferred that the casing is formed of a material which does not affect the growth of cells in cell culture. Examples of such materials include, for example, polymers such as polyethylene, polypropylene, nylon, polyester, polystyrene, polycarbonate, polymethyl methacrylate, polyethylene terephthalate; metals such as stainless steel, titanium, but not limited thereto.

Having some strength in the casing prevents the shape of the porous polymer film inside the casing from continually being changed, and thus the effect of the present invention will be better exhibited. In this specification, "the casing is not deformed" means that the casing is not absolutely undeformable but is deformed under load experienced in the ordinary culture environment.

The cell culture module is contained within the casing with:

(i) the two or more independent porous polymer films being aggregated;

(ii) the porous polymer films being folded up;

(iii) the porous polymer films being wound into a roll-like shape; and/or (iv) the porous polymer film being tied together into a rope-like shape.

In this specification, "two or more independent porous polymer films are aggregated and contained within a casing" means that two or more independent porous polymer films are aggregated and contained in a predetermined space surrounded by a casing. According to the present invention, the two or more independent porous polymer films may be immovably fixed by fixing at least one point of the porous polymer film to at least one point of the casing by an arbitrary method. In addition, the two or more independent porous polymer films may be fragments. The fragments may take any shape such as a circle, an ellipse, a square, a triangle, a polygon, a string, etc., but a substantially square shape is preferred. In the present invention, the fragments may be any size. When it has a substantially square shape, the side may be any length, but, for example, preferably 80 mm or less, preferably 50 mm or less, more preferably 30 mm or less, still more preferably 20 mm or less, and may be 10 mm or less. In addition, when the fragments of the porous polymer film are substantially square, it may be formed so that length of each side may match the inner wall or may be shorter than each side of the inner wall (e.g. shorter by about 0.1 mm to 1 mm), rendering the porous polymer film immovable in the casing. This can protect cells growing in the porous polymer film from stress to be applied, resulting in suppression of apoptosis or the like and enabling a stable cell culture in a large amount. The string-like porous polymer film may be contained within the casing, with: (ii) the porous polymer films being folded up; (iii) the porous polymer films being wound into a roll-like shape; and/or (iv) the porous polymer film being tied together into a rope-like shape, as described below. In addition, any number of the porous polymer films may be stacked to aggregate and contain the 2 or more independent porous polymer films in the casing. In this case, a liner may be provided between the porous polymer films. Providing a liner may enable efficient supply of a medium between the stacked porous polymer films. The liner may be not particularly limited so long as it may have function to form an arbitrary space between the stacked porous polymer films to efficiently supply medium. For example, a planar construct having a mesh structure may be used. As for material of the liner, for example, a mesh made of polystyrene, polycarbonate, polymethyl methacrylate, polyethylene terephthalate, stainless steel or the like may be used without limitation. When there is a liner having a mesh structure, the material may be appropriately selected so long as the mesh may have openings such that a medium may be supplied between the stacked porous polymer films.

In this specification, "the porous polymer films being folded up" means a porous polymer film which is folded up in the casing, and thus it is rendered immovable in the casing by frictional force between each surfaces of the porous polymer film and/or the inner surface of the casing. In this specification, "being folded" may indicate the pours polymer film being creased or creaseless.

In this specification, "the porous polymer films being wound into a roll-like shape" means the porous polymer film being wound into a roll-like shape and thus it is rendered immovable in the casing by frictional force between each surfaces of the porous polymer film and/or the inner surface of the casing. Moreover, in the present invention, the porous polymer film being tied together into a rope-like shape means, for example, more than one porous polymer films in rectangle strip shape are knitted into a rope-shape by arbitrary method, rendering the porous polymer films immovable by the mutual frictional force of the porous polymer films. It is also possible that (i) the two or more independent porous polymer films being aggregated; (ii) the porous polymer films being folded up; (iii) the porous polymer films being wound into a roll-like shape; and/or (iv) the porous polymer film being tied together into a rope-like shape may be combined and contained within a casing.

In this specification, "the porous polymer film being immovable in the casing" means that the porous polymer film is contained in the casing so that the porous polymer film is continually morphologically unchanged during culturing the cell culture module in the cell culture medium. In other words, the porous polymer film itself is continually prevented from waving by fluid. Since the porous polymer film is kept immovable in the casing, the cell growing in the porous polymer film is protected from stress to be applied, enabling stable cell culture without cells being killed by apoptosis.

As for the cell culture module of the invention, the commercially available product may be applied so long as it is a culture device, system etc. which may culture cells. For example, it is applicable to a culture device wherein a culture vessel is composed of a flexible bag, and can be used while it is suspended in the culture vessel. In addition, the cell culture module of the invention can be applied to and cultured in an agitating culture type vessel such as a spinner flask. In addition, as for a culture vessel, it may be applicable to an open type vessel, or it may be applicable to a closed type vessel. For example, any of a dish, a flask, plastic bag, test tube and large tank for cell culture may be used, as appropriate. These include, for example, Cell Culture Dish manufactured by BD Falcon, and Nunc Cell Factory manufactured by Thermo Scientific.

2. Application of Cell Culture Module to Cell Culture Device

In this specification, "cell culture device" is a term generally used synonymously for a cell culture system, bioreactor or reactor, and interchangeably used. The cell culture module of the invention is applicable to the cell culture device illustrated below. In addition, it is applicable to the commercially available devices other than devices illustrated below.

(1) Siphon Type Culture Device

Figure 9:
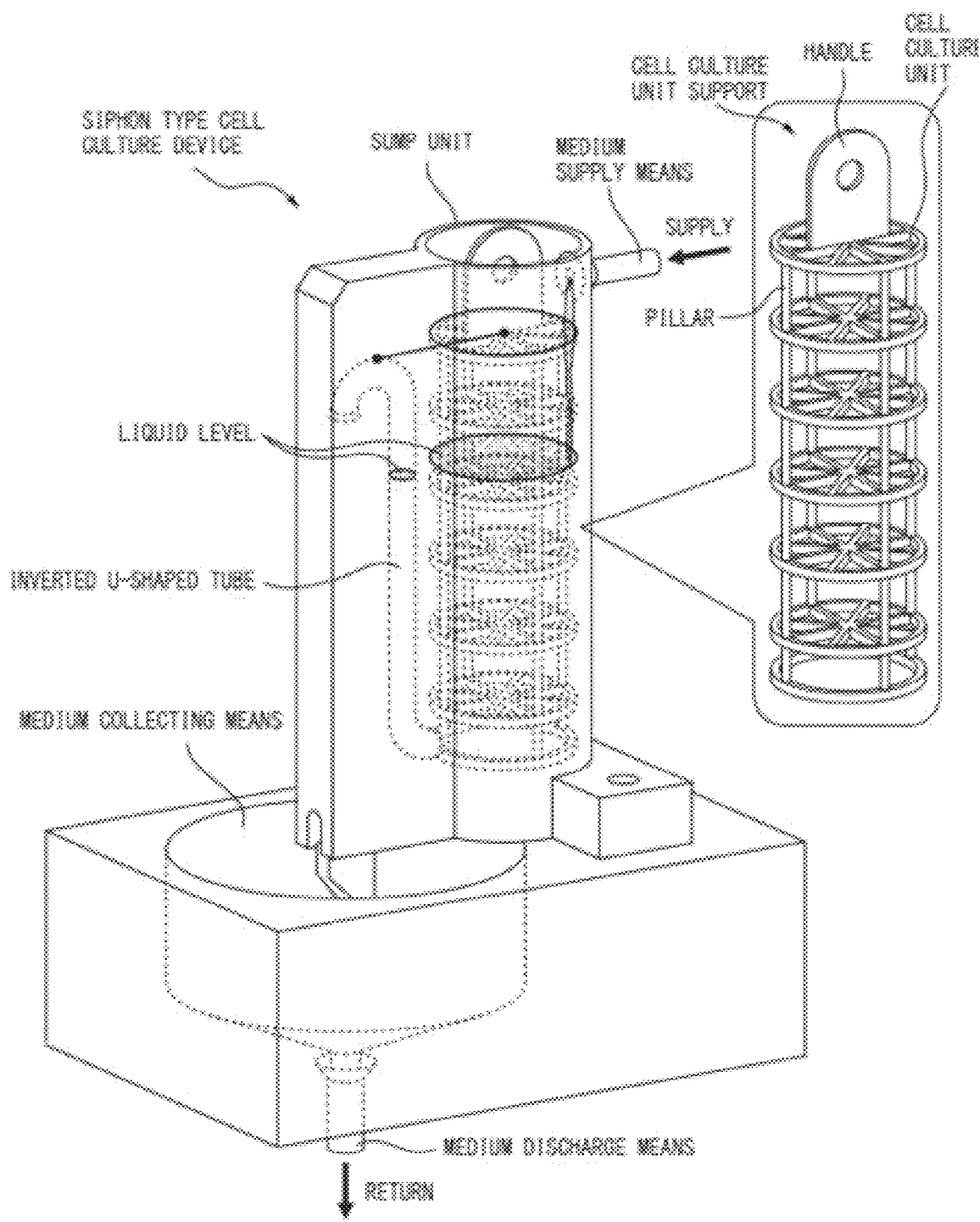
FIG. 9 represents an embodiment of a cell culture device used in Example 2.
Figure 24:
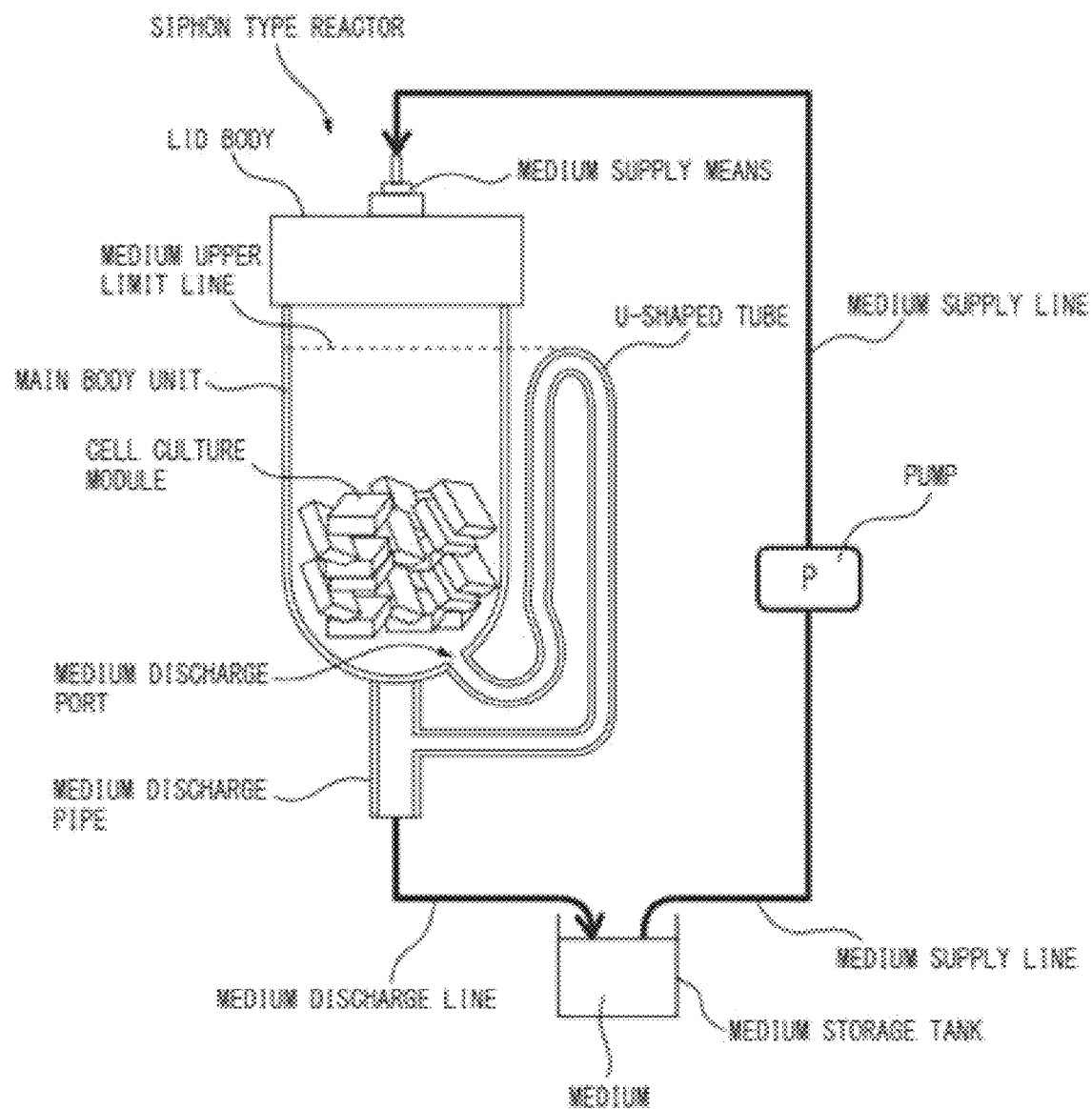
FIG. 24 is a diagram illustrating a dry heat sterilization type, siphon type cell culture device (heat resistant siphon type reactor) in an embodiment.

The cell culture module of the invention is applicable to a siphon type culture device depicted in FIGS. 9 and 24. A siphon type culture device is a cell culture device which is characterized by including a porous polymer film, a cell culture unit containing the porous polymer film, a sump unit containing the cell culture unit therein, a medium supply means placed at the upper part of the sump unit, an inverted U-shaped tube communicating with the bottom of the sump unit, a medium collecting means placed at the lower part of the other end of the inverted U-shaped tube, and a medium discharge means placed in the medium collecting means; wherein the porous polymer film is a three-layer structure porous polymer film having a surface layer A and a surface layer B, the surface layers having a plurality of pores, and a macrovoid layer sandwiched between the surface layers A and B; wherein an average pore diameter of the pores present in the surface layer A is smaller than an average pore diameter of the pores present in the surface layer B; wherein the macrovoid layer has a partition wall bonded to the surface layers A and B, and a plurality of macrovoids surrounded by such a partition wall and the surface layers A and B; wherein the pores in the surface layers A and B communicate with the macrovoid; and wherein when the liquid level of the medium supplied into the sump unit from the medium supply means reaches the top of the inverted U-shape tube, the medium is intermittently discharged into the medium collecting means by the principle of siphon. The device can be used wherein the porous polymer film is exchanged with the cell culture module.

(2) Cylindrical Type Vapor Phase Culture Device

Figure 11:
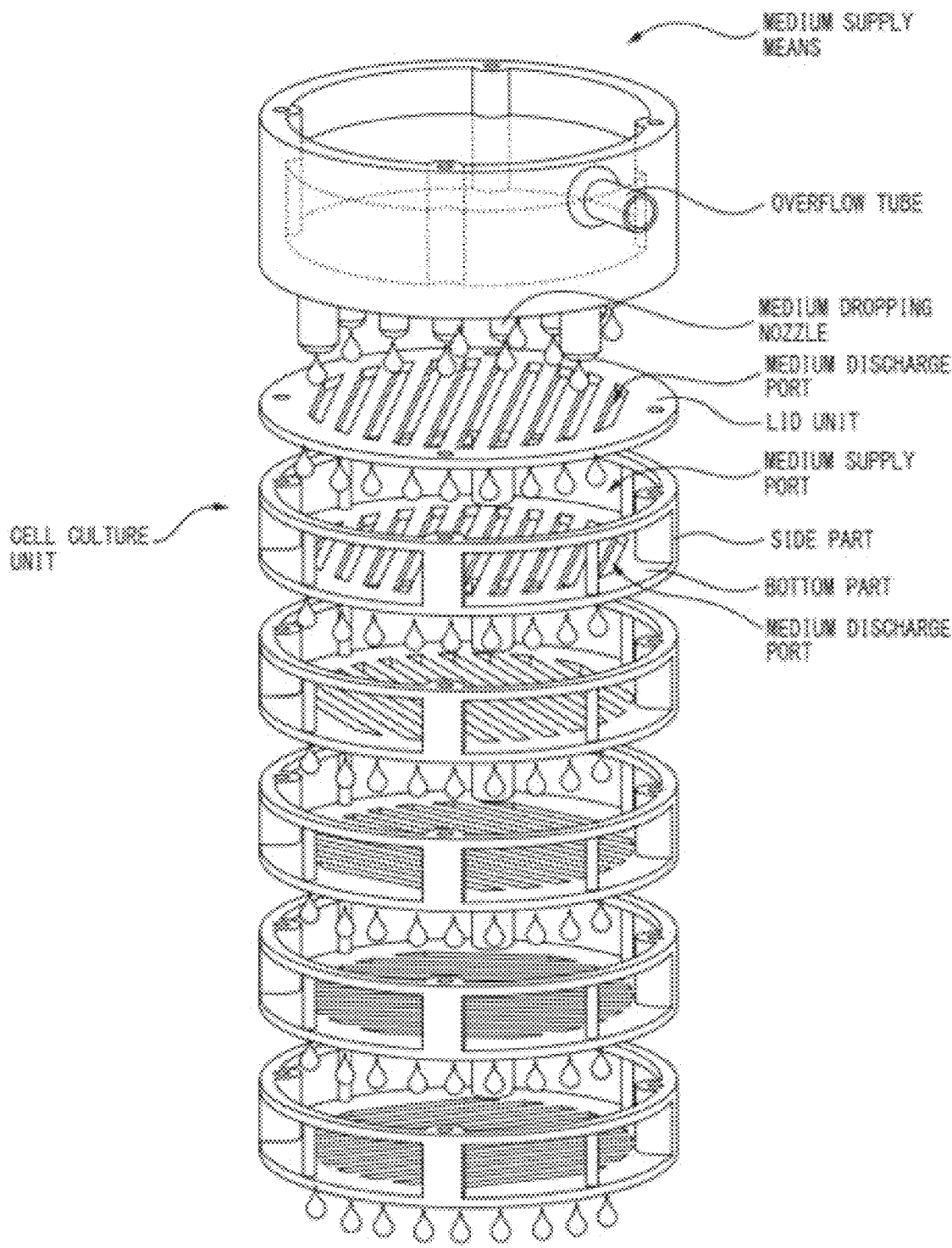
FIG. 11 represents an embodiment of a cell culture device used in Example 6. The embodiment has a structure which facilitates discharge of medium owing to medium discharge ports of the respective stages being displaced in counter-clockwise direction by 30 degree, with a basic construction being common to that in FIG. 10.
Figure 21:
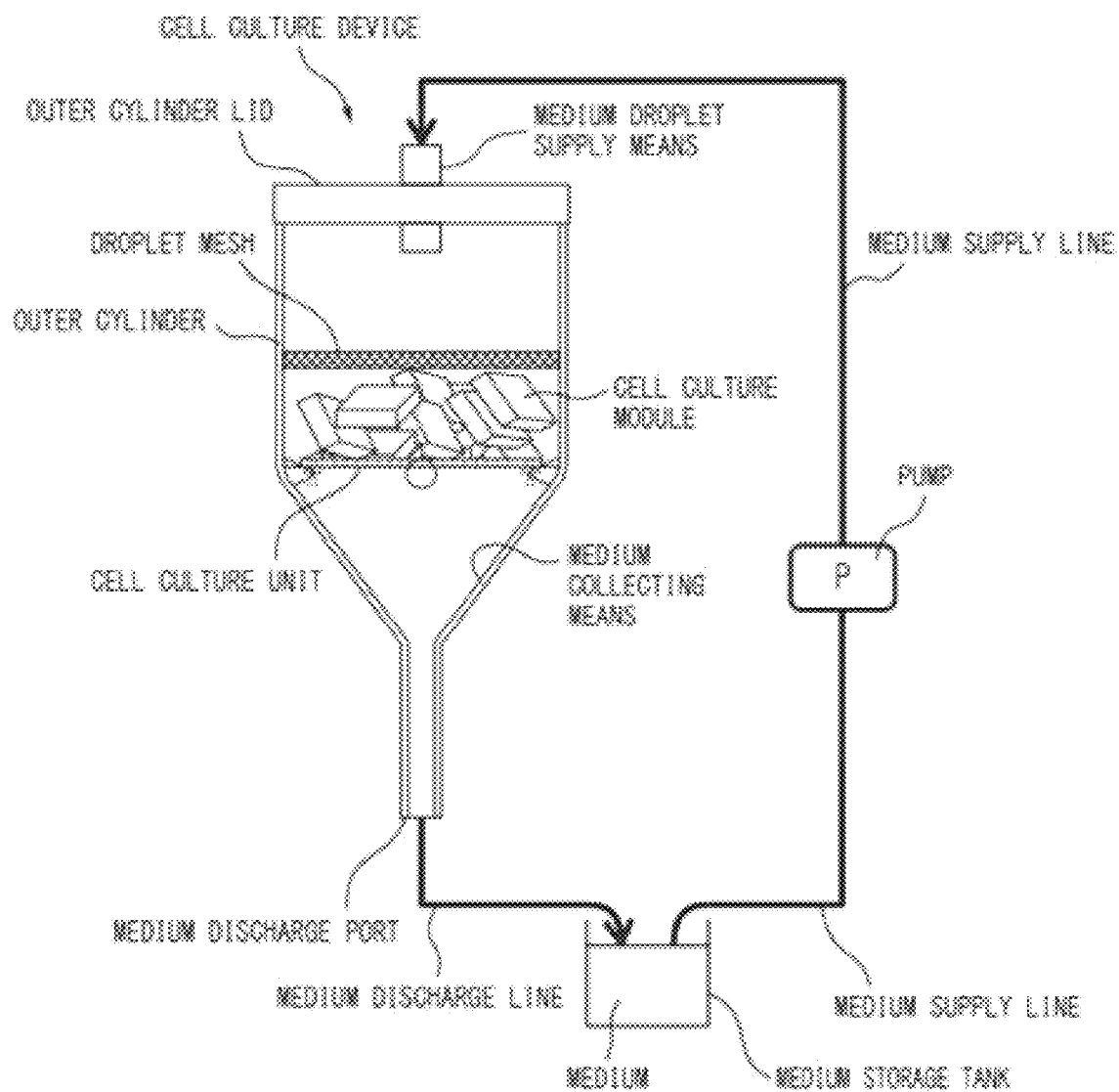
FIG. 21 represents a diagram illustrating a cell culture device in an embodiment.

The cell culture module of the present invention is applicable to a cylindrical type vapor phase culture device depicted in FIGS. 10, 11 and 21. In an embodiment, a cylindrical vapor phase culture device is a cell culture device which includes a porous polymer film, a cell culture unit containing the porous polymer film, a medium supply means placed at the upper part of the cell culture unit, and a medium collecting means placed at the lower part of the cell culture unit; wherein the porous polymer film is a three-layer structure porous polymer film having a surface layer A and a surface layer B, the surface layers having a plurality of pores, and a macrovoid layer sandwiched between the surface layers A and B; wherein an average pore diameter of the pores present in the surface layer A is smaller than an average pore diameter of the pores present in the surface layer B; wherein the macrovoid layer has a partition wall bonded to the surface layers A and B, and a plurality of macrovoids surrounded by such a partition wall and the surface layers A and B; wherein the cell culture unit is provided with a bottom part having one or more medium discharge port(s) and a side part arranged substantially vertical to the bottom part. In addition, in an embodiment, a cylindrical vapor phase culture device is a cell culture device which includes a porous polymer film, a cell culture unit containing the porous polymer film, a medium supply means placed at the upper part of the cell culture unit, and a medium collecting means placed at the lower part of the cell culture unit; wherein the porous polymer film is a three-layer structure porous polymer film having a surface layer A and a surface layer B, the surface layers having a plurality of pores, and a macrovoid layer sandwiched between the surface layers A and B; wherein an average pore diameter of the pores present in the surface layer A is smaller than an average pore diameter of the pores present in the surface layer B; wherein the macrovoid layer has a partition wall bonded to the surface layers A and B, and a plurality of macrovoids surrounded by such a partition wall and the surface layers A and B; wherein the pores in the surface layers A and B communicate with the macrovoid; and wherein the medium collecting means is a part of the outer cylinder containing the cell culture unit. The device can be used wherein the porous polymer film is exchanged with the cell culture module.

(3) Mist/Shower Type Culture Device

Figure 12:
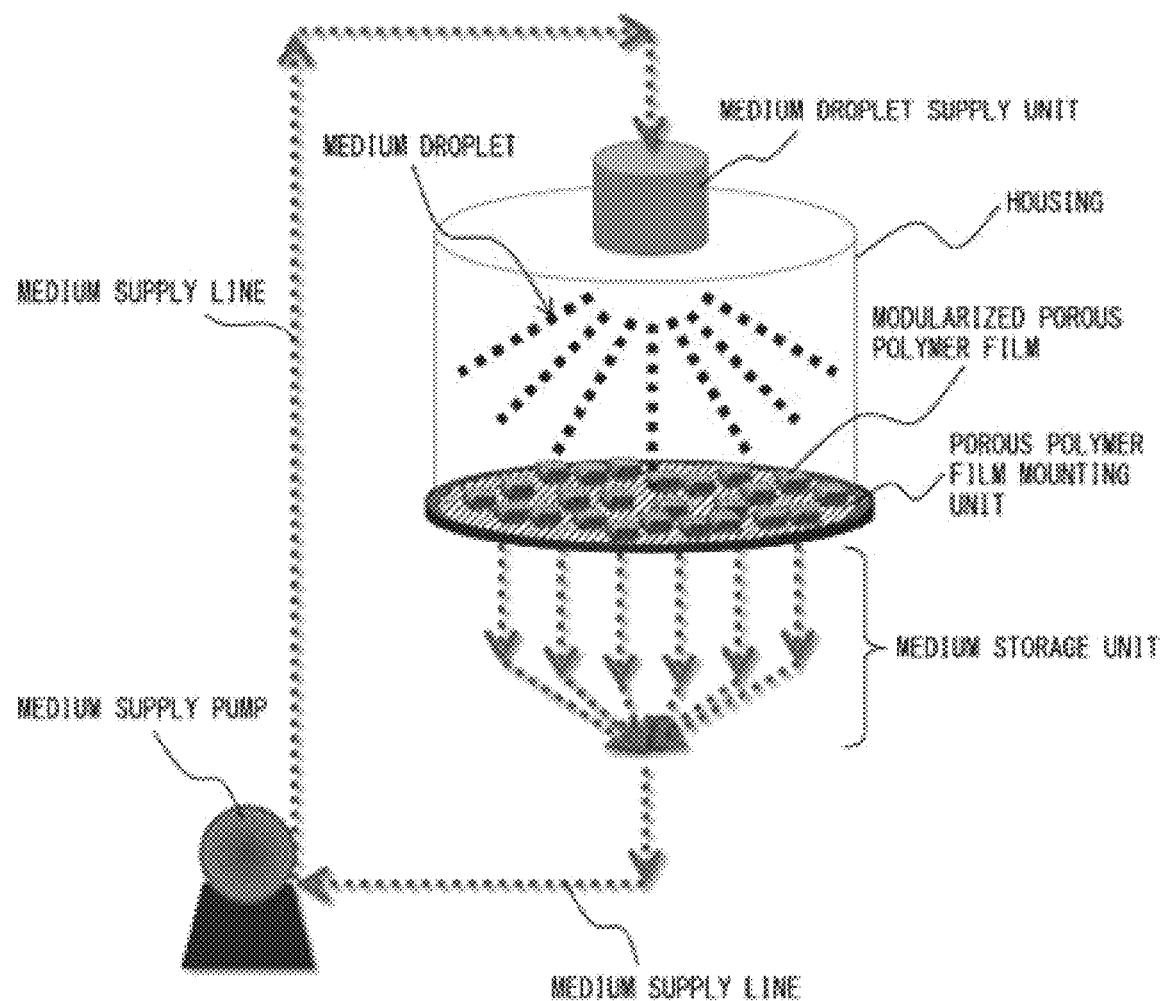
FIG. 12 represents an embodiment of a cell culture device used in Example 7.

The cell culture module of the present invention is applicable to a mist/shower type culture device depicted in FIG. 12. A mist/shower type culture device is a cell culture device which includes:

a porous polymer film, a porous polymer film mounting unit on which the porous polymer film is mounted, a housing containing the porous polymer film mounting unit, a medium droplet supply unit placed in the housing, a medium supply line communicating with the medium droplet supply unit, a medium storage unit communicating with the medium supply line, and a pump provided on a part of the medium supply line;

wherein the porous polymer film is a three-layer structure porous polymer film having a surface layer A and a surface layer B, the surface layers having a plurality of pores, and a macrovoid layer sandwiched between the surface layers A and B; wherein an average pore diameter of the pores present in the surface layer A is smaller than an average pore diameter of the pores present in the surface layer B; wherein the macrovoid layer has a partition wall bonded to the surface layers A and B, and a plurality of macrovoids surrounded by such a partition wall and the surface layers A and B; wherein the pores in the surface layers A and B communicate with the macrovoid; and wherein the porous polymer film mounting unit includes a plurality of slit- or mesh-like medium discharge ports. The device can be used wherein the porous polymer film is exchanged with the cell culture module.

(4) Vapor Phase Exposed Type Rotating Culture Device

Figure 13:
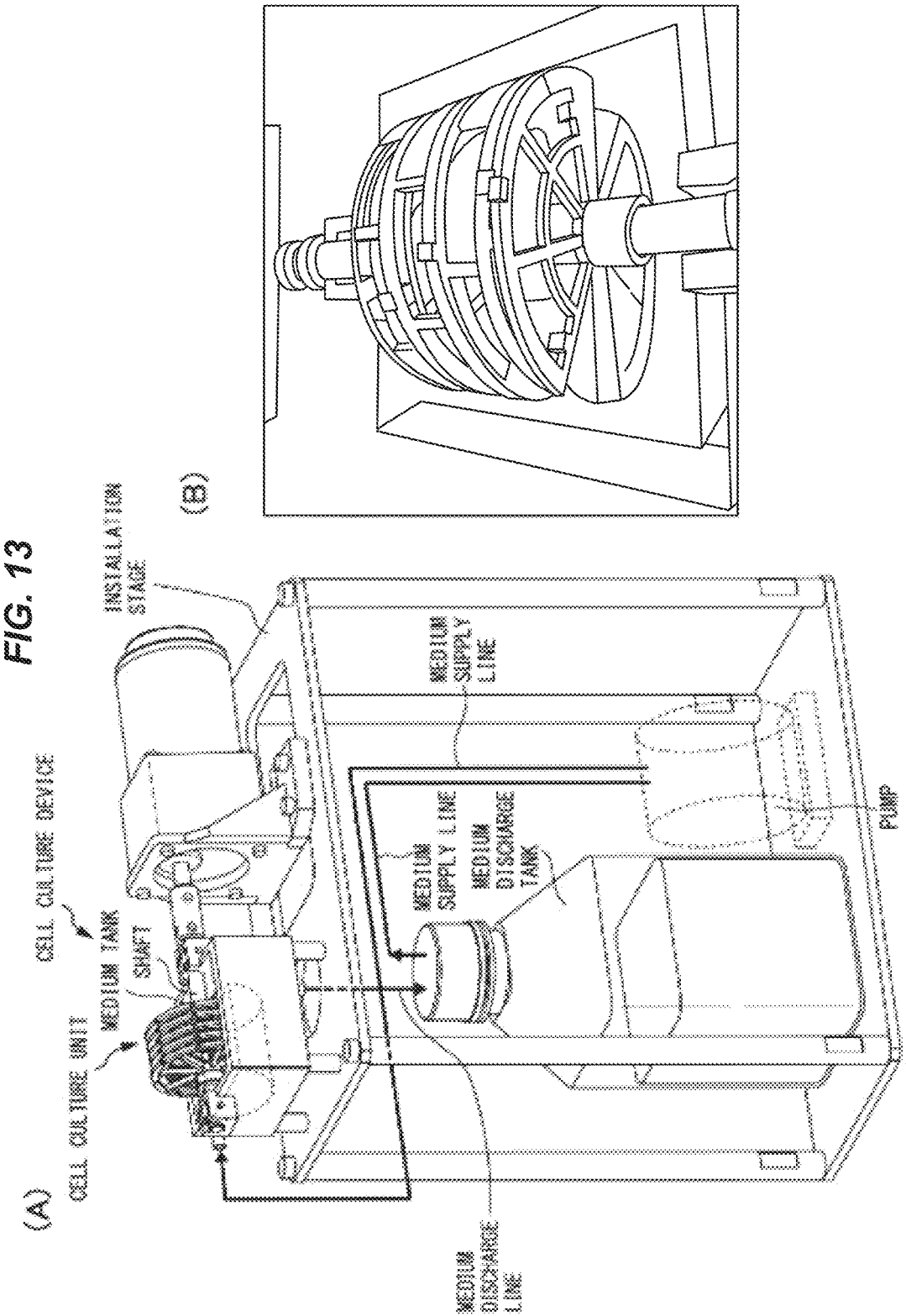
FIG. 13 represents an embodiment of a cell culture device used in Example 9. (A) represents a construction of a cell culture device. (B) is a diagram illustrating a cylindrical vessel (without a spiral flow channel) used in Example 9.
Figure 14:
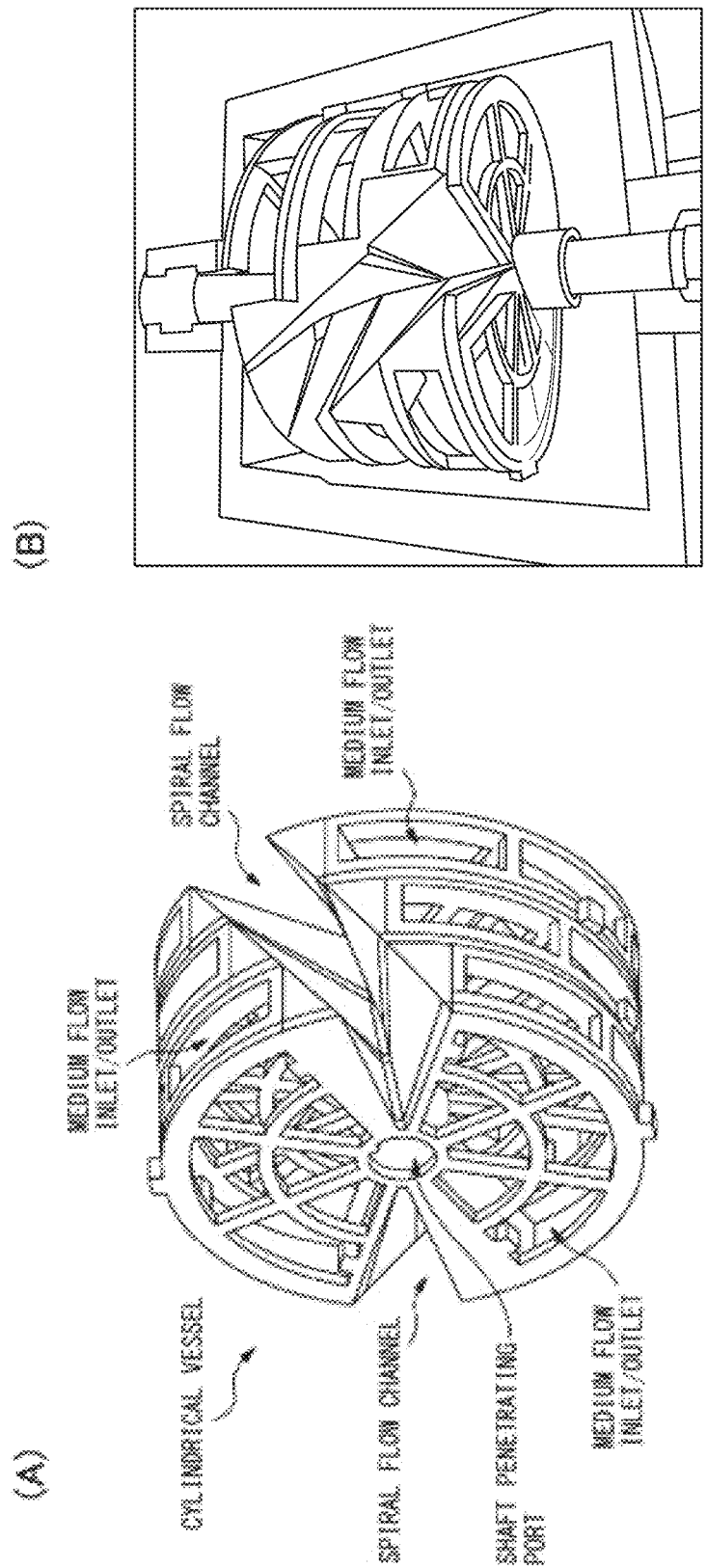
FIG. 14 represents an embodiment of a cell culture device used in Example 10. (A) is a schematic diagram illustrating a cylindrical vessel (with a spiral flow channel) used in Example 10. (B) is a diagram illustrating a cylindrical vessel (with a spiral flow channel) used in Example 10.

The cell culture module of the invention is applicable to a rotating culture device depicted in FIGS. 13, 14 and 20. The vapor phase exposed type rotating culture device includes:

the cell culture device includes a porous polymer film, a cell culture unit having the porous polymer film, a shaft penetrating the cell culture unit, a rotating motor to rotate the shaft; and a medium tank immersing at least a part of the cell culture unit;

wherein the porous polymer film is a three-layer structure porous polymer film having a surface layer A and a surface layer B, the surface layers having a plurality of pores, and a macrovoid layer sandwiched between the surface layers A and B; wherein an average pore diameter of the pores present in the surface layer A is smaller than an average pore diameter of the pores present in the surface layer B; wherein the macrovoid layer has a partition wall bonded to the surface layers A and B, and a plurality of macrovoids surrounded by such a partition wall and the surface layers A and B; wherein the pores in the surface layers A and B communicate with the macrovoid; and wherein the cell culture unit rotates around the shaft, and the cells supported on the porous polymer film are cultured alternately in a vapor phase and a liquid phase. The device can be used wherein the porous polymer film is exchanged with the cell culture module.

3. Porous Polymer Film

An average pore diameter of the pore present on a surface layer A (hereinafter referred to as "surface A" or "mesh surface") in the porous polymer film used for the present invention is not particularly limited, but is, for example, 0.01 μm or more and less than 200 μm, 0.01 to 150 μm, 0.01 to 100 μm, 0.01 to 50 μm, 0.01 to 40 μm, 0.01 to 30 μm, 0.01 to 20 μm, or 0.01 to 15 μm, preferably 0.01 to 15 μm.

The average pore diameter of the pore present on a surface layer B (hereinafter referred to as "surface B" or "large pore surface") in the porous polymer film used for the present invention is not particularly limited so long as it is larger than the average pore diameter of the pore present on the surface A, but is, for example, greater than 5 μm and 200 μm or less, 20 μm to 100 μm, 30 μm to 100 μm, 40 μm to 100 μm, 50 μm to 100 μm, or 60 μm to 100 μm, preferably 20 μm to 100 μm.

The average pore diameter on the surface of the porous polymer film is determined by measuring pore area for 200 or more open pore portions, and calculated an average diameter according to the following Equation (1) from the average pore area assuming the pore shape as a perfect circle.

[Math. 1]

$$\text{Average Pore Diameter} = 2 \times \sqrt{(Sa/\pi)} \quad (1)$$

(wherein Sa represents the average value for the pore areas)

The thicknesses of the surface layers A and B are not particularly limited, but is, for example, 0.01 to 50 µm, preferably 0.01 to 20 µm.

The average pore diameter of macrovoids in the planar direction of the film in the macrovoid layer in the porous polymer film is not particularly limited but is, for example, 10 to 500 µm, preferably 10 to 100 µm, and more preferably 10 to 80 µm. The thicknesses of the partition wall in the macrovoid layer are not particularly limited, but is, for example, 0.01 to 50 µm, preferably 0.01 to 20 µm. In an embodiment, at least one partition wall in the macrovoid layer has one or two or more pores connecting the neighboring macrovoids and having the average pore diameter of 0.01 to 100 µm, preferably 0.01 to 50 µm. In another embodiment, the partition wall in the macrovoid layer has no pore.

The total film thickness of the porous polymer film used for the invention is not particularly limited, but may be 5 µm or more, 10 µm or more, 20 µm or more or 25 µm or more, and 500 µm or less, 300 µm or less, 100 µm or less, 75 µm or less, or 50 µm or less. It is preferably 5 to 500 µm, and more preferably 25 to 75 µm.

The film thickness of the porous polymer film used for the invention can be measured using a contact thickness gauge.

The porosity of the porous polymer film used in the present invention is not particularly limited but is, for example, 40% or more and less than 95%.

The porosity of the porous polymer film used for the invention can be determined by measuring the film thickness and mass of the porous film cut out to a prescribed size, and performing calculation from the basis weight according to the following Equation (2).

[Math. 2]

$$\text{Porosity (\%)} = (1 - w/(S \times d \times D)) \times 100 \quad (2)$$

(wherein S represents the area of the porous film, d represents the total film thickness, w represents the measured mass, and D represents the polymer density. The density is defined as 1.34 g/cm³ when the polymer is a polyimide.)

The porous polymer film used for the present invention is preferably a porous polymer film which includes a three-layer structure porous polymer film having a surface layer A and a surface layer B, the surface layers having a plurality of pores, and a macrovoid layer sandwiched between the surface layers A and B; wherein the average pore diameter of the pore present on the surface layer A is 0.01 µm to 15 µm, and the average pore diameter of the pore present on the surface layer B is 20 µm to 100 µm; wherein the macrovoid layer has a partition wall bonded to the surface layers A and B, and a plurality of macrovoids surrounded by such a partition wall and the surface layers A and B, the thickness of the macrovoid layer, and the surface layers A and B is 0.01 to 20 µm; wherein the pores on the surface layers A and B communicate with the macrovoid, the total film thickness is 5 to 500 µm, and the porosity is 40% or more and less than 95%. In an embodiment, at least one partition wall in the macrovoide layer has one or two or more pores connecting the neighboring macrovoids with each other and having the average pore diameter of 0.01 to 100 µm, preferably 0.01 to 50 µm. In another embodiment, the partition wall does not have such pores.

The porous polymer film used for the present invention is preferably sterilized. The sterilization treatment is not particularly limited, but any sterilization treatment such as dry heat sterilization, steam sterilization, sterilization with a disinfectant such as ethanol, electromagnetic wave sterilization such as ultraviolet rays or gamma rays, and the like can be mentioned.

The porous polymer film used for the present invention is not particularly limited so long as it has the structural features described above and includes, preferably a porous polyimide film or porous polyethersulfone film.

3-1. Porous Polyimide Film

Polyimide is a general term for polymers containing imide bonds in the repeating unit, and usually it refers to an aromatic polyimide in which aromatic compounds are directly linked by imide bonds. An aromatic polyimide has an aromatic-aromatic conjugated structure via an imide bond, and therefore has a strong rigid molecular structure, and since the imide bonds provide powerful intermolecular force, it has very high levels of thermal, mechanical and chemical properties.

The porous polyimide film usable for the present invention is a porous polyimide film preferably containing polyimide (as a main component) obtained from tetracarboxylic dianhydride and diamine, more preferably a porous polyimide film composed of tetracarboxylic dianhydride and diamine. The phrase "including as the main component" means that it essentially contains no components other than the polyimide obtained from a tetracarboxylic dianhydride and a diamine, as constituent components of the porous polyimide film, or that it may contain them but they are additional components that do not affect the properties of the polyimide obtained from the tetracarboxylic dianhydride and diamine.

In an embodiment, the porous polyimide film usable for the present invention includes a colored porous polyimide film obtained by forming a polyamic acid solution composition including a polyamic acid solution obtained from a tetracarboxylic acid component and a diamine component, and a coloring precursor, and then heat treating it at 250° C. or higher.

A polyamic acid is obtained by polymerization of a tetracarboxylic acid component and a diamine component. A polyamic acid is a polyimide precursor that can be cyclized to a polyimide by thermal imidization or chemical imidization.

The polyamic acid used may be any one that does not have an effect on the invention, even if a portion of the amic acid is imidized. Specifically, the polyamic acid may be partially thermally imidized or chemically imidized.

When the polyamic acid is to be thermally imidized, there may be added to the polyamic acid solution, if necessary, an imidization catalyst, an organic phosphorus-containing compound, or fine particles such as inorganic fine particles or organic fine particles. In addition, when the polyamic acid is to be chemically imidized, there may be added to the polyamic acid solution, if necessary, a chemical imidization agent, a dehydrating agent, or fine particles such as inorganic fine particles or organic fine particles. Even if such components are added to the polyamic acid solution, they are preferably added under conditions that do not cause precipitation of the coloring precursor.

In this specification, a "coloring precursor" is a precursor that generates a colored substance by partial or total carbonization under heat treatment at 250° C. or higher.

Coloring precursors usable for the production of the porous polyimide film are preferably uniformly dissolved or dispersed in a polyamic acid solution or polyimide solution and subjected to thermal decomposition by heat treatment at 250° C. or higher, preferably 260° C. or higher, even more preferably 280° C. or higher and more preferably 300° C. or higher, and preferably heat treatment in the presence of oxygen such as air, at 250° C., preferably 260° C. or higher, even more preferably 280° C. or higher and more preferably 300° C. or higher, for carbonization to produce a colored substance, more preferably producing a black colored substance, with carbon-based coloring precursors being most preferred.

The coloring precursor, when being heated, first appears as a carbonized compound, but compositionally it contains other elements in addition to carbon, and also includes layered structures, aromatic crosslinked structures and tetrahedron carbon-containing disordered structures.

Carbon-based coloring precursors are not particularly restricted, and for example, they include tar or pitch such as petroleum tar, petroleum pitch, coal tar and coal pitch, coke, polymers obtained from acrylonitrile-containing monomers, ferrocene compounds (ferrocene and ferrocene derivatives), and the like. Of these, polymers obtained from acrylonitrile-containing monomers and/or ferrocene compounds are preferred, with polyacrylonitrile being preferred as a polymer obtained from an acrylonitrile-containing monomer.

Moreover, in another embodiment, examples of the porous polyimide film which may be used for the preset invention also include a porous polyimide film which can be obtained by molding a polyamic acid solution derived from a tetracarboxylic acid component and a diamine component followed by heat treatment without using the coloring precursor.

The porous polyimide film produced without using the coloring precursor may be produced, for example, by casting a polyamic acid solution into a film, the polyamic acid solution being composed of 3 to 60% by mass of polyamic acid having an intrinsic viscosity number of 1.0 to 3.0 and 40 to 97% by mass of an organic polar solvent, immersing or contacting in a coagulating solvent containing water as an essential component, and imidating the porous film of the polyamic acid by heat treatment. In this method, the coagulating solvent containing water as an essential component may be water, or a mixed solution containing 5% by mass or more and less than 100% by mass of water and more than 0% by mass and 95% by mass or less of an organic polar solvent. Further, after the imidation, one surface of the resulting porous polyimide film may be subjected to plasma treatment.

The tetracarboxylic dianhydride which may be used for the production of the porous polyimide film may be any tetracarboxylic dianhydride, selected as appropriate according to the properties desired. Specific examples of tetracarboxylic dianhydrides include biphenyltetracarboxylic dianhydrides such as pyromellitic dianhydride, 3,3',4,4'-biphenyltetracarboxylic dianhydride (s-BPDA) and 2,3,3',4'-biphenyltetracarboxylic dianhydride (a-BPDA), oxydiphthalic dianhydride, diphenylsulfone-3,4,3',4'-tetracarboxylic dianhydride, bis(3,4-dicarboxyphenyl)sulfide dianhydride, 2,2-bis(3,4-dicarboxyphenyl)-1,1,1,3,3,3-hexafluoropropane dianhydride, 2,3,3',4'-benzophenonetetracarboxylic dianhydride, 3,3',4,4'-benzophenonetetracarboxylic dianhydride, bis(3,4-dicarboxyphenyl)methane dianhydride, 2,2-bis(3,4-dicarboxyphenyl)propane dianhydride, p-phenylenebis(trimellitic acid monoester acid anhydride), p-biphenylenebis(trimellitic acid monoester acid anhydride), m-terphenyl-3,4,3',4'-tetracarboxylic dianhydride, p-terphenyl-3,4,3',4'-tetracarboxylic dianhydride, 1,3-bis(3,4-dicarboxyphenoxy)benzene dianhydride, 1,4-bis(3,4-dicarboxyphenoxy)benzene dianhydride, 1,4-bis(3,4-dicarboxyphenoxy)biphenyl dianhydride, 2,2-bis[(3,4-dicarboxyphenoxy)phenyl]propane dianhydride, 2,3,6,7-naphthalenetetracarboxylic dianhydride, 1,4,5,8-naphthalenetetracarboxylic dianhydride, 4,4'-(2,2-hexafluoroisopropylidene)diphthalic dianhydride, and the like. Also preferably used is an aromatic tetracarboxylic acid such as 2,3,3',4'-diphenylsulfonetetracarboxylic acid. These may be used alone or in appropriate combinations of two or more.

Particularly preferred among these are at least one type of aromatic tetracarboxylic dianhydride selected from the group consisting of biphenyltetracarboxylic dianhydride and pyromellitic dianhydride. As a biphenyltetracarboxylic dianhydride there may be suitably used 3,3',4,4'-biphenyltetracarboxylic dianhydride.

As diamine which may be used for the production of the porous polyimide film, any diamine may be used. Specific examples of diamines include the following.

1) Benzenediamines with one benzene nucleus, such as 1,4-diaminobenzene(paraphenylenediamine), 1,3-diaminobenzene, 2,4-diaminotoluene and 2,6-diaminotoluene;

2) diamines with two benzene nuclei, including diaminodiphenyl ethers such as 4,4'-diaminodiphenyl ether and 3,4'-diaminodiphenyl ether, and 4,4'-diaminodiphenylmethane, 3,3'-dimethyl-4,4'-diaminobiphenyl, 2,2'-dimethyl-4,4'-diaminobiphenyl, 2,2'-bis(trifluoromethyl)-4,4'-diaminobiphenyl, 3,3'-dimethyl-4,4'-diaminodiphenylmethane, 3,3'-dicarboxy-4,4'-diaminodiphenylmethane, 3,3',5,5'-tetramethyl-4,4'-diaminodiphenylmethane, bis(4-aminophenyl)sulfide, 4,4'-diaminobenzanilide, 3,3'-dichlorobenzidine, 3,3'-dimethylbenzidine, 2,2'-dimethylbenzidine, 3,3'-dimethoxybenzidine, 2,2'-dimethoxybenzidine, 3,3'-diaminodiphenyl ether, 3,4'-diaminodiphenyl ether, 4,4'-diaminodiphenyl ether, 3,3'-diaminodiphenyl sulfide, 3,4'-diaminodiphenyl sulfide, 4,4'-diaminodiphenyl sulfide, 3,3'-diaminodiphenylsulfone, 3,4'-diaminodiphenylsulfone, 4,4'-diaminodiphenylsulfone, 3,3'-diaminobenzophenone, 3,3'-diamino-4,4'-dichlorobenzophenone, 3,3'-diamino-4,4'-dimethoxybenzophenone, 3,3'-diaminodiphenylmethane, 3,4'-diaminodiphenylmethane, 4,4'-diaminodiphenylmethane, 2,2-bis(3-aminophenyl)propane, 2,2-bis(4-aminophenyl)propane, 2,2-bis(3-aminophenyl)-1,1,1,3,3,3-hexafluoropropane, 2,2-bis(4-aminophenyl)-1,1,1,3,3,3-hexafluoropropane, 3,3'-diaminodiphenyl sulfoxide, 3,4'-diaminodiphenyl sulfoxide and 4,4'-diaminodiphenyl sulfoxide;

3) diamines with three benzene nuclei, including 1,3-bis(3-aminophenyl)benzene, 1,3-bis(4-aminophenyl)benzene, 1,4-bis(3-aminophenyl)benzene, 1,4-bis(4-aminophenyl)benzene, 1,3-bis(4-aminophenoxy)benzene, 1,4-bis(3-aminophenoxy)benzene, 1,4-bis(4-aminophenoxy)benzene, 1,3-bis(3-aminophenoxy)-4-trifluoromethylbenzene, 3,3'-diamino-4-(4-phenyl)phenoxybenzophenone, 3,3'-diamino-4,4'-di(4-phenylphenoxy)benzophenone, 1,3-bis(3-aminophenyl sulfide)benzene, 1,3-bis(4-aminophenyl sulfide)benzene, 1,4-bis(4-aminophenyl sulfide)benzene, 1,3-bis(3-aminophenylsulfone)benzene, 1,3-bis(4-aminophenylsulfone)benzene, 1,4-bis(4-aminophenylsulfone)benzene, 1,3-bis[2-(4-aminophenyl)isopropyl]benzene, 1,4-bis

[2-(3-aminophenyl)isopropyl]benzene and 1,4-bis[2-(4-aminophenyl)isopropyl]benzene;

4) diamines with four benzene nuclei, including 3,3'-bis(3-aminophenoxy)biphenyl, 3,3'-bis(4-aminophenoxy)biphenyl, 4,4'-bis(3-aminophenoxy)biphenyl, 4,4'-bis(4-aminophenoxy)biphenyl, bis[3-(3-aminophenoxy)phenyl]ether, bis[3-(4-aminophenoxy)phenyl] ether, bis[4-(3-aminophenoxy)phenyl]ether, bis[4-(4-aminophenoxy)phenyl]ether, bis[3-(3-aminophenoxy)phenyl]ketone, bis[3-(4-aminophenoxy)phenyl]ketone, bis[4-(3-aminophenoxy)phenyl]ketone, bis[4-(4-aminophenoxy)phenyl]ketone, bis[3-(3-aminophenoxy)phenyl]sulfide, bis[3-(4-aminophenoxy)phenyl]sulfide, bis[4-(3-aminophenoxy)phenyl] sulfide, bis[4-(4-aminophenoxy)phenyl] sulfide, bis[3-(3-aminophenoxy)phenyl] sulfone, bis[3-(4-aminophenoxy)phenyl]sulfone, bis[4-(3-aminophenoxy)phenyl]sulfone, bis[4-(4-aminophenoxy)phenyl]sulfone, bis[3-(3-aminophenoxy)phenyl]methane, bis[3-(4-aminophenoxy)phenyl]methane, bis[4-(3-aminophenoxy)phenyl]methane, bis[4-(4-aminophenoxy)phenyl]methane, 2,2-bis[3-(3-aminophenoxy)phenyl]propane, 2,2-bis[3-(4-aminophenoxy)phenyl]propane, 2,2-bis[4-(3-aminophenoxy)phenyl]propane, 2,2-bis[4-(4-aminophenoxy)phenyl]propane, 2,2-bis[3-(3-aminophenoxy)phenyl]-1,1,1,3,3,3-hexafluoropropane, 2,2-bis[3-(4-aminophenoxy)phenyl]-1,1,1,3,3,3-hexafluoropropane, 2,2-bis[4-(3-aminophenoxy)phenyl]-1,1,1,3,3,3-hexafluoropropane and 2,2-bis[4-(4-aminophenoxy)phenyl]-1,1,1,3,3,3-hexafluoropropane.

These may be used alone or in mixtures of two or more. The diamine used may be appropriately selected according to the properties desired.

Preferred among these are aromatic diamine compounds, with 3,3'-diaminodiphenyl ether, 3,4'-diaminodiphenyl ether, 4,4'-diaminodiphenyl ether, paraphenylenediamine, 1,3-bis(3-aminophenyl)benzene, 1,3-bis(4-aminophenyl)benzene, 1,4-bis(3-aminophenyl)benzene, 1,4-bis(4-aminophenyl)benzene, 1,3-bis(4-aminophenoxy)benzene and 1,4-bis(3-aminophenoxy)benzene being preferred for use. Particularly preferred is at least one type of diamine selected from the group consisting of benzenediamines, diaminodiphenyl ethers and bis(aminophenoxy)phenyl.

From the viewpoint of heat resistance and dimensional stability under high temperature, the porous polyimide film which may be used for the invention is preferably formed from a polyimide obtained by combination of a tetracarboxylic dianhydride and a diamine, having a glass transition temperature of 240° C. or higher, or without a distinct transition point at 300° C. or higher.

From the viewpoint of heat resistance and dimensional stability under high temperature, the porous polyimide film which may be used for the invention is preferably a porous polyimide film comprising one of the following aromatic polyimides.

(i) An aromatic polyimide comprising at least one tetracarboxylic acid unit selected from the group consisting of biphenyltetracarboxylic acid units and pyromellitic acid units, and an aromatic diamine unit, (ii) an aromatic polyimide comprising a tetracarboxylic acid unit and at least one type of aromatic diamine unit selected from the group consisting of benzenediamine units, diaminodiphenyl ether units and bis(aminophenoxy)phenyl units, and/or, (iii) an aromatic polyimide comprising at least one type of tetracarboxylic acid unit selected from the group consisting of biphenyltetracarboxylic acid units and pyromellitic acid units, and at least one type of aromatic diamine unit selected from the group consisting of benzenediamine units, diaminodiphenyl ether units and bis(aminophenoxy)phenyl units.

The porous polyimide film used in the present invention is preferably a three-layer structure porous polyimide film having a surface layer A and a surface layer B, the surface layers having a plurality of pores, and a macrovoid layer sandwiched between the surface layers A and B; wherein an average pore diameter of the pores present in the surface layer A is 0.01 μm to 15 μm, and the mean pore diameter present on the surface layer B is 20 μm to 100 μm; wherein the macrovoid layer has a partition wall bonded to the surface layers A and B, and a plurality of macrovoids surrounded by such a partition wall and the surface layers A and B; wherein the thickness of the macrovoid layer, and the surface layers A and B is 0.01 to 20 μm, wherein the pores on the surface layers A and B communicate with the macrovoid, the total film thickness is 5 to 500 μM, and the porosity is 40% or more and less than 95%. In this case, at least one partition wall in the macrovoid layer has one or two or more pores connecting the neighboring macrovoids and having the average pore diameter of 0.01 to 100 μm, preferably 0.01 to 50 μm.

For example, porous polyimide films described in WO2010/038873, Japanese Unexamined Patent Publication (Kokai) No. 2011-219585 or Japanese Unexamined Patent Publication (Kokai) No. 2011-219586 may be used for the present invention.

3-2. Porous Polyethersulfone Film (Porous PES Film)

The porous polyethersulfone film which may be used for the present invention contains polyethersulfone and typically consists substantially of polyethersulfone. Polyethersulfone may be synthesized by the method known to those skilled in the art. For example, it may be produced by a method wherein a dihydric phenol, an alkaline metal compound and a dihalogenodiphenyl compound are subjected to polycondensation reaction in an organic polar solvent, a method wherein an alkaline metal di-salt of a dihydric phenol previously synthesized is subjected to polycondensation reaction dihalogenodiphenyl compound in an organic polar solvent or the like.

Examples of an alkaline metal compound include alkaline metal carbonate, alkaline metal hydroxide, alkaline metal hydride, alkaline metal alkoxide and the like. Particularly, sodium carbonate and potassium carbonate are preferred.

Examples of a dihydric phenol compound include hydroquinone, catechol, resorcin, 4,4'-biphenol, bis (hydroxyphenyl)alkanes (such as 2,2-bis(hydroxyphenyl)propane, and 2,2-bis(hydroxyphenyl)methane), dihydroxydiphenylsulfones, dihydroxydiphenyl ethers, or those mentioned above having at least one hydrogen on the benzene rings thereof substituted with a lower alkyl group such as a methyl group, an ethyl group, or a propyl group, or with a lower alkoxy group such as a methoxy group, or an ethoxy group. As the dihydric phenol compound, two or more of the aforementioned compounds may be mixed and used.

Polyethersulfone may be a commercially available product. Examples of a commercially available product include SUMIKAEXCEL 7600P, SUMIKAEXCEL 5900P (both manufactured by Sumitomo Chemical Company, Limited).

The logarithmic viscosity of the polyethersulfone is preferably 0.5 or more, more preferably 0.55 or more from the viewpoint of favorable formation of a macrovoid of the porous polyethersulfone membrane; and it is preferably 1.0 or less, more preferably 0.9 or less, further preferably 0.8 or less, particularly preferably 0.75 or less from the viewpoint of the easy production of a porous polyethersulfone film.

Further, from the viewpoints of heat resistance and dimensional stability under high temperature, it is preferred that the porous polyethersulfone film or polyethersulfone as a raw material thereof has a glass transition temperature of 200° C. or higher, or that a distinct glass transition temperature is not observed.

The method for producing the porous polyethersulfone film which may be used for the present invention is not particularly limited. For example, the film may be produced by a method including the following steps:

a step in which polyethersulfone solution containing 0.3 to 60% by mass of polyethersulfone having logarithmic viscosity of 0.5 to 1.0 and 40 to 99.7% by mass of an organic polar solvent is casted into a film, immersed in or contacted with a coagulating solvent containing a poor solvent or non-solvent of polyethersulfone to produce a coagulated film having pores; and a step in which the coagulated film having pores obtained in the above-mentioned step is heat-treated for coarsening of the aforementioned pores to obtain a porous polyethersulfone film;

wherein the heat treatment includes the temperature of the coagulated film having the pores is raised higher than the glass transition temperature of the polyethersulfone, or up to 240° C. or higher.

The porous polyethersulfone film which can be used in the present invention is preferably a porous polyethersulfone film having a surface layer A, a surface layer B, and a macrovoid layer sandwiched between the surface layers A and B, wherein the macrovoid layer has a partition wall bonded to the surface layers A and B, and a plurality of macrovoids surrounded by such a partition wall and the surface layers A and B, the macrovoids having the average pore diameter in the planar direction of the film of 10 to 500 µm;

wherein the thickness of the macrovoid layer is 0.1 to 50 µm, each of the surface layers A and B has a thickness of 0.1 to 50 µm, wherein one of the surface layers A and B has a plurality of pores having the average pore diameter of more than 5 µm and 200 µm or less, while the other has a plurality of pores having the average pore diameter of 0.01 µm or more and less than 200 µm, wherein one of the surface layers A and B has a surface aperture ratio of 15% or more while other has a surface aperture ratio of 10% or more, wherein the pores of the surface layers A and B communicate with the macrovoids, wherein the porous polyethersulfone film has total film thickness of 5 to 500 µm and a porosity of 50 to 95%.

4. Cell Culture Method Using Cell Culture Module

An embodiment of the present invention is a method for culturing cell, which includes the following steps:

(1) applying a cell culture module to a first medium containing a cell in a cell suspension;

(2) maintaining a temperature at which the cell can be cultured, and adsorbing the cell to the cell culture module, and (3) culturing the cell culture module having the cell adsorbed thereto, in a second medium in a culture vessel;

wherein the cell culture module comprising:

a porous polymer film; and a casing having two or more medium flow inlets, the casing containing the porous polymer film, wherein the porous polymer film is a three-layer structure porous polymer film having a surface layer A and a surface layer B, the surface layers having a plurality of pores, and a macrovoid layer sandwiched between the surface layers A and B; wherein an average pore diameter of the pores present in the surface layer A is smaller than an average pore diameter of the pores present in the surface layer B; wherein the macrovoid layer has a partition wall bonded to the surface layers A and B, and a plurality of macrovoids surrounded by such a partition wall and the surface layers A and B;

wherein the porous polymer film is contained within the casing with:

the two or more independent porous polymer films being aggregated;

(ii) the porous polymer films being folded up;

(iii) the porous polymer films being wound into a roll-like shape; and/or (iv) the porous polymer film being tied together into a rope-like shape;

wherein no surfactant is contained in the second medium. The method for cell culture of the present invention will be hereinafter referred to as a "cell culture method of the invention".

The types of the cells which may be used for the present invention may be selected from the group consisting of animal cells, insect cells, plant cells, yeast cells and bacteria. Animal cells are largely divided into cells from animals belonging to the subphylum Vertebrata, and cells from non-vertebrates (animals other than animals belonging to the subphylum Vertebrata). There are no particular restrictions on the source of the animal cells, for the purpose of the present specification. Preferably, they are cells from an animal belonging to the subphylum Vertebrata. The subphylum Vertebrata includes the superclass Agnatha and the superclass Gnathostomata, the superclass Gnathostomata including the class Mammalia, the class Ayes, the class *Amphibia* and the class Reptilia. Preferably, they are cells from an animal belonging to the class Mammalia, generally known as mammals. Mammals are not particularly restricted but include, preferably, mice, rats, humans, monkeys, pigs, dogs, sheep and goats.

The types of animal cells or plant cells that may be used for the invention are not particularly restricted, but are preferably selected from the group consisting of pluripotent stem cells, tissue stem cells, somatic cells and germ cells.

The term "pluripotent stem cells", in this specification, is intended as a comprehensive term for stem cells having the ability to differentiate into cells of any tissues (pluripotent differentiating power). While not restrictive, pluripotent stem cells include embryonic stem cells (ES cells), induced pluripotent stem cells (iPS cells), embryonic germ cells (EG cells) and germ stem cells (GS cells). They are preferably ES cells or iPS cells. Particularly preferred are iPS cells, which are free of ethical problems, for example. The pluripotent stem cells used may be any publicly known ones, and for example, the pluripotent stem cells described in WO2009/123349 (PCT/JP2009/057041) may be used.

The term "tissue stem cells" refers to stem cells that are cell lines capable of differentiation but only to limited specific tissues, though having the ability to differentiate into a variety of cell types (pluripotent differentiating power). For example, hematopoietic stem cells in the bone marrow are the source of blood cells, while neural stem cells differentiate into neurons. Additional types include hepatic stem cells from which the liver is formed and skin stem cells that form skin tissue. Preferably, the tissue stem cells are selected from among mesenchymal stem cells, hepatic stem cells, pancreatic stem cells, neural stem cells, skin stem cells and hematopoietic stem cells.

The term "somatic cells" refers to cells other than germ cells, among the cells composing a multicellular organism. In sexual reproduction, these are not passed on to the next generation. Preferably, the somatic cells are selected from among hepatocytes, pancreatic cells, muscle cells, bone cells, osteoblasts, osteoclasts, chondrocytes, adipocytes, skin cells, fibroblasts, pancreatic cells, renal cells and lung cells, or blood cells such as lymphocytes, erythrocytes, leukocytes, monocytes, macrophages or megakaryocytes.

The term "germ cells" refers to cells having the role of passing on genetic information to the succeeding generation in reproduction. These include, for example, gametes for sexual reproduction, i.e. the ova, egg cells, sperm, sperm cells, and spores for asexual reproduction.

The cells may also be selected from the group consisting of sarcoma cells, established cell lines and transformants. The term "sarcoma" refers to cancer occurring in non-epithelial cell-derived connective tissue cells, such as the bone, cartilage, fat, muscle or blood, and includes soft tissue sarcomas, malignant bone tumors and the like. Sarcoma cells are cells derived from sarcoma. The term "established cell line" refers to cultured cells that are maintained in vitro for long periods and reach a stabilized character and can be semi-permanently subcultured. Cell lines derived from various tissues of various species including humans exist, such as PC12 cells (from rat adrenal medulla), CHO cells (from Chinese hamster ovary), HEK293 cells (from human embryonic kidney), HL-60 cells (from human leukocytes) and HeLa cells (from human cervical cancer), Vero cells (from African green monkey kidney epithelial cells), MDCK cells (from canine renal tubular epithelial cells), HepG2 cells (from human hepatic cancer), BHK cells (new-born hamster kidney cell), NIH3T3 cells (from mouse fetal fibroblast cells). The term "transformants" refers to cells with an altered genetic nature by extracellularly introduced nucleic acid (DNA and the like).

In this specification, an "adherent cell" is generally a cell which is required to adhere itself on an appropriate surface for growth, and is also referred to as an adhesion cell or an anchorage-dependent cell. In certain embodiments of the present invention, the cells used are adherent cells. The cells used for the present invention are adherent cells, more preferably cells which may be cultured even as a suspension in a medium. The adherent cells which can be suspension cultured may be obtained by conditioning the adherent cells to a state suitable for suspension culture, and include, for example, CHO cells, HEK293 cells, Vero cells, NIH3T3 cells, and cell lines derived from these cells. The cells used for the present invention other than listed herein are not particularly limited so long that they may be applied to suspension culture by conditioning.

Figure 7:
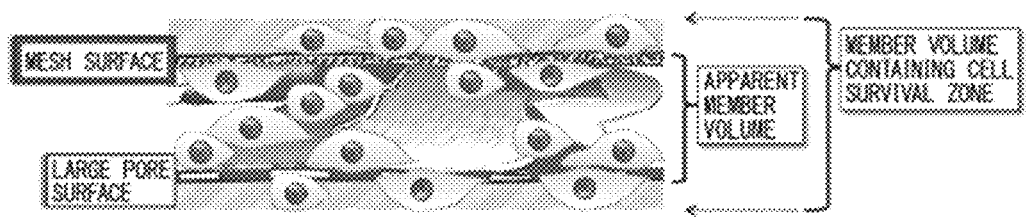
FIG. 7 represents a model diagram of cell culturing using a porous polyimide film.
Figure 8:
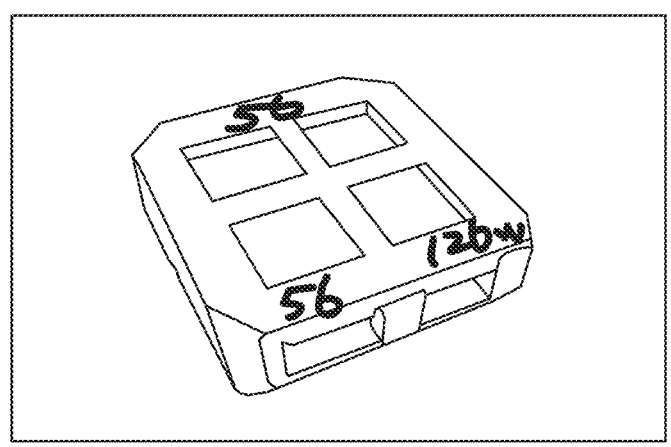
FIG. 8 represents an embodiment of a cell culture module used in Example 1.

FIG. 7 represents a model diagram of cell culturing using a porous polymer film. FIG. 7 serves merely for illustration and the elements are not drawn to their actual dimensions. In the cell culture method of the invention, application of cells and culturing are carried out on a porous polymer film, thereby allowing culturing of large volumes of cells to be accomplished since large numbers of cells grow on the multisided connected pore sections on the inside, and the surfaces on the porous polymer film. Moreover, in the cell culture method of the invention, it is possible to culture large volumes of cells while drastically reducing the amount of medium used for cell culturing compared to the prior art. For example, large volumes of cells can be cultured even when all or a portion of the porous polymer film is not in contact with the liquid phase of the cell culture medium. In addition, the total volume of the cell culture medium in the cell culture vessel, with respect to the total porous polymer film volume including the cell survival zone, can be significantly reduced.

Throughout the present specification, the volume of the porous polymer film without cells, that occupies the space including the volume between the interior gaps, will be referred to as the "apparent porous polymer film volume" (see, FIG. 7). In the state where the cells are applied to the porous polymer film and the cells have been supported on the surface and the interior of the porous polymer film, the total volume of the porous polymer film, the cells and the medium that has wetted the porous polymer film interior, which is occupying the space therein, will be referred to as the "porous polymer film volume including the cell survival zone" (see, FIG. 1). When the porous polymer film has a film thickness of 25 μm, the porous polymer film volume including the cell survival zone is a value of at maximum about 50% larger than the apparent porous polymer film volume. In the method of the invention, a plurality of porous polymer films may be housed in a single cell culture vessel for culturing, in which case the total sum of the porous polymer film volume including the cell survival zone for each of the plurality of porous polymer films supporting the cells may be referred to simply as the "total sum of the porous polymer film volume including the cell survival zone".

Using the method of the invention, cells can be satisfactorily cultured for a long period of time even under conditions in which the total volume of the cell culture medium in the cell culture vessel is 10,000 times or less of the total sum of the porous polymer film volume including the cell survival zone. Moreover, cells can be satisfactorily cultured for a long period of time even under conditions in which the total volume of the cell culture medium in the cell culture vessel is 1,000 times or less of the total sum of the porous polymer film volume including the cell survival zone. In addition, cells can be satisfactorily cultured for a long period of time even under conditions in which the total volume of the cell culture medium in the cell culture vessel is 100 times or less of the total sum of the porous polymer film volume including the cell survival zone. In addition, cells can be satisfactorily cultured for a long period of time even under conditions in which the total volume of the cell culture medium in the cell culture vessel is 10 times or less of the total sum of the porous polymer film volume including the cell survival zone.

In other words, according to the invention, the space (vessel) used for cell culturing can be reduced to an absolute minimum, compared to a conventional cell culture device for performing two-dimensional culture. Furthermore, when it is desired to increase the number of cells cultured, the cell culturing volume can be flexibly increased by a convenient procedure including increasing the number of layered porous polymer films. In a cell culture device comprising a porous polymer film to be used for the invention, the space (vessel) in which cells are cultured and the space (vessel) in which the cell culture medium is stored can be separate, and the necessary amount of cell culture medium can be prepared according to the number of cells to be cultured. The space (vessel) in which the cell culture medium is stored can be increased or decreased according to the purpose, or it may be a replaceable vessel, with no particular restrictions.

In the cell culture method of the invention, culturing in which the number of cells in the cell culture vessel after culturing using the porous polymer film reaches $1.0 \times 10^5$ or more, $1.0 \times 10^6$ or more, $2.0 \times 10^6$ or more, $5.0 \times 10^6$ or more, $1.0\times10^7$ or more, $2.0\times10^7$ or more, $5.0\times10^7$ or more, $1.0\times10^8$ or more, $2.0\times10^8$ or more, $5.0\times10^8$ or more, $1.0\times10^9$ or more, $2.0\times10^9$ or more, or $5.0\times10^9$ or more per milliliter of medium, assuming that all of the cells are evenly dispersed in the cell culture medium in the cell culture vessel, is mentioned.

It should be noted that as a method for measuring cell count during or after culture, various known methods may be used. For example, as the method for counting the number of cells in the cell culture vessel after culturing using the porous polymer film, assuming that the cells are evenly dispersed in the cell culture medium in the cell culture vessel, any publicly known method may be used. For example, a cell count method using CCK8 may be suitably used. Specifically, a Cell Counting Kit 8 (a solution reagent, commercially available from Dojindo Laboratories)(hereunder referred to as "CCK8") may be used to count the number of cells in ordinary culturing without using a porous polymer film, and the correlation coefficient between the absorbance and the actual cell count is determined. Subsequently, the cells are applied, the cultured porous polymer film may be transferred to CCK8-containing medium and stored in an incubator for 1 to 3 hours, and then the supernatant is extracted and its absorbance is measured at a wavelength of 480 nm, and the cell count is determined from the previously calculated correlation coefficient.

In addition, from another point of view, for example, "mass culturing of cells" may refer to culturing in which the number of cells in the cell culture vessel after culturing using the porous polyimide film reaches $1.0\times10^5$ or more, $2.0\times10^5$ or more, $1.0\times10^6$ or more, $2.0\times10^6$ or more, $5.0\times10^6$ or more, $1.0\times10^7$ or more, $2.0\times10^7$ or more or $5.0\times10^7$ or more, $1.0\times10^8$ or more, $2.0\times10^8$ or more, or $5.0\times10^8$ or more, per square centimeter of porous polymer film. The number of cells contained per square centimeter of porous polymer film may be appropriately measured using a publicly known method, such as with a cell counter.

In this specification, a "cell in a cell suspension" encompasses a cell obtained by forcing to suspend an adherent cell in a medium with a proteolytic enzyme such as trypsin, and cells which may be applied to suspension culture in a medium by the aforementioned conditioning step.

In this specification, a "medium" refers to a cell culture medium for culturing cells, especially animal cells. The term "medium" is interchangeably used as "cell culture solution". Accordingly, the medium used in the invention refers to a liquid medium. As for types of a medium, the conventionally used medium may be used and appropriately selected depending on the types of cells to be cultured.

In the cell culture method of the invention, the first medium used in the step (1) is not particularly limited so long as it may culture cells. For example, when CHO cells are cultured, BalanCD (Trademark) CHO GROWH A (manufactured by JX Energy) may be used.

In the cell culture method of the invention, a temperature at which cell culture may be performed in the step (2) may be any temperature at which cells may be adsorbed onto a cell culture module, for example 10 to 45° C., preferably 15 to 42° C., more preferably 20 to 40° C., still more preferably 25 to 39° C. In addition, in the cell culture method of the invention, a time for cells to be adsorbed in the step (2) is, for example, 5 minutes to 24 hours, preferably 10 minutes to 12 hours, more preferably 15 minutes to 500 minutes.

In the cell culture method of the invention, in the step (2), the cells may be adsorbed to the porous polymer film of the cell culture module with shaking and/or stirring, or cells may be adsorbed to the porous polymer film of the cell culture module while being stood still. The method for shaking is not particularly limited. For example, a culture vessel containing the cell culture module of the invention and cells is mounted and shaken on a commercially available shaking device. Shaking may be performed continuously or intermittently. For example, shaking and standing still are alternately repeated and adjusted as appropriate. The method for stirring is not particularly limited. For example, the cell culture module of the invention and cells are placed in a commercially available spinner flask and stirred by rotating a stirrer. Stirring may be performed continuously or intermittently. For example, stirring and standing still are alternately repeated and adjusted as appropriate.

In the cell culture method of the invention, as the second medium used in the step (3), a medium used for culturing adherent cells may be selected. For example, D-MEM, E-MEM, IMDM, Ham's F-12 and the like may be used, but not limited to them. The second medium is preferably a medium free from a component which prevents a cell from adhering to a substrate, such as a surfactant. The second medium used may be appropriately selected depending on the types of cells. In the step (3), culturing in the second medium facilitates the cells which is adsorbed onto the porous polymer film in the step (2) to adhere in the porous polymer film. Accordingly, cells may be stably cultured without being detached from the porous polymer film. In addition, the cell culture method of the invention utilizes the cell culture module provided with the porous polymer film described above. The cell culture module used in the cell culture method of the present invention can prevent continuing morphological deformation of the membrane-like porous polymer film within a casing because of containing a porous polymer film in the casing. This can protect cells to be grown in the porous polymer film from stress to be applied, resulting in suppression of apoptosis or the like and enabling a stable cell culture in a large amount.

In the cell culture method of the invention, the step (3) may utilize any commercially available product so long as it is a culture device and system which may culture cells. For example, the culture vessel may be a flexible bag-type culture vessel. In addition, culture may be performed in a stirring type culture vessel such as spinner flask as a culture vessel. In addition, an open type vessel may be applicable, and a closed type vessel may be applicable, as a culture vessel. For example, any of a dish, flask, plastic bag, test tube and large tank for cell culturing may be used, as appropriate. These include, for example, Cell Culture Dish manufactured by BD Falcon, and Nunc Cell Factory manufactured by Thermo Scientific. In addition, in the cell culture method, by using a cell culture module, it has become possible to carry out culturing even of cells that have not been capable of natural suspension culture, using a device intended for suspension culture, in a state similar to suspension culturing. The device for suspension culture that is used may be, for example, a spinner flask or rotating culturing flask manufactured by Corning, Inc. In addition, the step (3) may be performed in a cell culture device described in this specification.

In the cell culture method of the invention, the step (3) may be performed using a continuously circulating type device in which a medium is continuously added to and collected from a culture vessel containing the cell culture module.

In the cell culture method of the present invention, the step (3) may be a system in which cell culturing according to the invention may be carried out in a system in which a cell culture medium is continuously or intermittently supplied to a cell culture vessel from cell culture medium supply means installed outside of the cell culture vessel. In this case, the system may be such that the cell culture medium is circulated between the cell culture medium supply means and the cell culture vessel.

5. Method for Removing Cell from Cell Suspension

An embodiment of the present invention relates to a method for removing a cell from a cell suspension, which includes:

(1) applying a porous polymer film to a first medium containing the cell;

(2) maintaining a temperature at which the cell can be cultured and allowing the cell to be adsorbed onto the porous polymer film;

wherein the porous polymer film is a three-layer structure porous polymer film having a surface layer A and a surface layer B, the surface layers having a plurality of pores, and a macrovoid layer sandwiched between the surface layers A and B; wherein an average pore diameter of the pores present in the surface layer A is smaller than an average pore diameter of the pores present in the surface layer B; wherein the macrovoid layer has a partition wall bonded to the surface layers A and B, and a plurality of macrovoids surrounded by such a partition wall and the surface layers A and B. The method for removing a cell of the present invention will be referred to as "the method for cell removal of the invention".

As a porous polymer film used in the method for cell removal of the invention, the aforementioned porous polymer film may be used. The porous polymer film may be the aforementioned cell culture module, or a porous polymer film which is not contained in a casing.

In the cell culture method of the invention, the first medium used in the step (1) is not particularly limited so long as it may culture cells. For example, in the case of culturing CHO cell, BalanCD (Trademark) CHO GROWN A (manufactured by JX Energy) may be used.

In the method for removing the cell of the invention, a temperature at which cell culture may be performed in the step (2) may be any temperature at which cells may be adsorbed onto a cell culture module, for example 10 to 45° C., preferably 15 to 42° C., more preferably 20 to 40° C., still more preferably 25 to 39° C. In addition, in the cell culture method of the invention, a time for cells to be adsorbed in the step (2) is, for example, 5 minutes to 24 hours, preferably 10 minutes to 12 hours, more preferably 15 minutes to 500 minutes.

According to the method for cell removal of the invention, in the step (2), the cells may be adsorbed to the porous polymer film of the cell culture module with shaking and/or stirring, or cells may be adsorbed to the porous polymer film of the cell culture module while being stood still. The method for shaking is not particularly limited. For example, a culture vessel containing the cell culture module of the invention and cells is mounted and shaken on a commercially available shaking device. Shaking may be performed continuously or intermittently. For example, shaking and standing still are alternately repeated and adjusted as appropriate. The method for stirring is not particularly limited. For example, the cell culture module of the invention and cells are placed in a commercially available spinner flask and stirred by rotating a stirrer. Shaking may be performed continuously or intermittently. For example, stirring and standing still are alternately repeated and adjusted as appropriate.

According to the method for removing cells of the invention, the removal of cells from a medium containing cells has heretofore required process such as centrifugation or treatment with a filter. According to the method of the invention, it is possible to remove cells from a medium without using a filter or the like.

6. Method for Killing Cell in Suspension

An embodiment of the invention relates to a method for killing a cell in a cell suspension, the method comprising the steps of:

(1) applying a porous polymer film to a first medium containing the cell;

(2) maintaining a temperature at which the cell can be cultured, and allowing the cell to be adsorbed onto the porous polymer film; and (3) allowing the porous polymer film having the cell adsorbed therein to be suspended in a second medium in a culture vessel to culture the porous polymer film by continuously changing the morphology thereof;

wherein the porous polymer film is a three-layer structure porous polymer film having a surface layer A and a surface layer B, the surface layers having a plurality of pores, and a macrovoid layer sandwiched between the surface layers A and B; wherein an average pore diameter of the pores present in the surface layer A is smaller than an average pore diameter of the pores present in the surface layer B; wherein the macrovoid layer has a partition wall bonded to the surface layers A and B, and a plurality of macrovoids surrounded by such a partition wall and the surface layers A and B; wherein the pores in the surface layers A and B communicate with the macrovoid; and wherein no surfactant is contained in the second medium. The method for killing cells of the invention is hereinafter referred to as a "method for cell killing of the invention".

The porous polymer film used for the method for cell killing of the invention is same as described above. The porous polymer film used in the cell killing method of the invention is a porous polymer film which is not contained in the casing, unlike the cell culture module and cell culture method described above.

In the cell killing method of the invention, the first medium used in the step (1) is not particularly limited so long as it may culture cells. For example, when a CHO cell is cultured, BalanCD (Trademark) CHO GROWH A (manufactured by JX Energy) may be used.

In the cell killing method of the invention, a temperature at which cell culture may be performed in the step (2) may be any temperature at which cells may be adsorbed onto a porous polymer film, for example 10 to 45° C., preferably 15 to 42° C., more preferably 20 to 40° C., still more preferably 25 to 39° C. In addition, in the cell killing method of the invention, a time for cells to be adsorbed in the step (2) is, for example, 5 minutes to 24 hours, preferably 10 minutes to 12 hours, more preferably 15 minutes to 500 minutes.

In the method of cell killing of the invention, by including the step (3) which allows the porous polymer film having the cell adsorbed therein to be suspended in a second medium in a culture vessel to culture the porous polymer film by continuously changing the morphology thereof, cells in the porous polymer film are killed by apoptosis etc. In the cell culture method of the invention, as the second medium used in the step (3), a medium used for culturing of adherent cells may be selected. For example, D-MEM, E-MEM, IMDM, Ham's F-12 and the like may be used, but not limited to them. The second medium is preferably a medium free from a component which prevents a cell from adhering to a substrate, such as a surfactant. The second medium used may be appropriately selected depending on the types of cells. In the step (3), culturing in the second medium facilitates the cells which is adsorbed onto the porous polymer film in the step (2) to adhere in the porous polymer film.

In the cell killing method of the invention, the step (3) may be at any temperature, for example 10 to 45° C., preferably 15 to 42° C., more preferably 20 to 40° C., still more preferably 25 to 39° C. The method for cell killing of the invention makes it possible to destroy cells without using a surfactant which is used in the conventional cell killing method, especially in the method for disrupting cell membrane.

EXAMPLES

The present invention will now be explained in greater detail by Examples. It is to be understood, however, that the invention is not limited to these Examples. A person skilled in the art may easily implement modifications and changes to the invention based on the description in the present specification, and these are also encompassed within the technical scope of the invention.

The porous polyimide films used in the following examples were prepared by forming a polyamic acid solution composition including a polyamic acid solution obtained from 3,3',4,4'-biphenyltetracarboxylic dianhydride (s-BPDA) as a tetracarboxylic acid component and 4,4'-diaminodiphenyl ether (ODA) as a diamine component, and polyacrylamide as a coloring precursor, and performing heat treatment at 250° C. or higher. The resulting porous polyimide film was a three-layer structure porous polyimide film having a surface layer A and a surface layer B, the surface layers having a plurality of pores, and a macrovoid layer sandwiched between the surface layers A and B; wherein the average pore diameter of the pore present on the surface layer A was 6 μm, the average pore diameter of the pore present on the surface layer B was 46 μm, and the film thickness was 25 μm, and the porosity was 73%.

Example 1

Cell Culture Using Bag-Type Module Reactor

Conditioned/suspended anti-human IL-8 antibody producing CHO-DP12 cells (ATCC CRL-12445) were suspension-cultured using a medium (BalanCD (Trademark) CHO Growth A) and culture was continued until viable cell count per mL was $1.6 \times 10^6$. A box-type module (FIG. 8) was prepared, and a 25 μm porous polyimide film was installed aseptically in the module in various combination illustrated below, and a lid portion of the box was welded to complete preparation of the module. The configuration of each experiment is illustrated in Table 1. The size of the porous polyimide film used is 1.5×1.5 cm.

TABLE 1

Configuration of Module in Experiment

| Experiment | Configuration of Module | Number of Module Area of Member | Number of Seeded Cells | Remarks |
|---|---|---|---|---|
| 1 | 20 pieces (10 pieces/ Partition/10 pieces) | 1 45 cm² | $1.6 \times 10^7$ | None |
| 2 | 20 pieces (10 pieces/ Partition/10 pieces) | 2 45 cm² | $1.6 \times 10^7$ | Notched Porous Polyimide Film |

TABLE 1-continued

Configuration of Module in Experiment

| Experiment | Configuration of Module | Number of Module Area of Member | Number of Seeded Cells | Remarks |
|---|---|---|---|---|
| 3 | 20 pieces (10 pieces/ Partition/10 pieces) | 2 90 cm² | $1.6 \times 10^7$ | None |
| 4 | 20 pieces (10 pieces/ Partition/10 pieces) | 3 135 cm² | $1.6 \times 10^7$ | None |
| 5 | 40 pieces (10 pieces/ Partition/10 pieces/ Partition/10 pieces/ Partition/10 pieces) | 1 90 cm² | $1.2 \times 10^7$ | None |

As described in Table 1, 1 to 3 modules were placed in an oxygen permeable bag for shaking culture, and shaking culture was performed overnight in a $CO_2$ incubator. Next day, a culture solution containing cells were discharged from each shaking bag, and measured cell count. The result of cell collection in each experiment is illustrated in Table 2 below. It was confirmed that the adhered cell count varied depending on the sheet area and accumulation condition of the porous polyimide film.

TABLE 2

The result of the collected cells in Experiment

| | Experiment No. | | | | |
|---|---|---|---|---|---|
| | 1 | 2 | 3 | 4 | 5 |
| Number of Collected Cell | $7.0 \times 10^6$ | $5.4 \times 10^6$ | $4.0 \times 10^6$ | $3.6 \times 10^6$ | $5.7 \times 10^6$ |
| Cell Collecting Rate | 44% | 34% | 25% | 23% | 36% |

A fresh medium (20 mL) was poured and shaking culture was continued in a $CO_2$ incubator. A medium was exchanged once every 2 to 3 days, cell count was determined by colorimetric quantification with a Cell Counting Kit 8 (a solution reagent, manufactured by Dojindo Laboratories) (hereunder referred to as "CCK8") as required, and an amount of the produced antibody was determined by HPLC method. The medium maintained a clear state. The results of culture 6 days and 8 days after removal of a suspension are illustrated in Tables 3 and 4. In both cases, an amount of medium was 20 mL. As a medium, IMDM supplemented with 2% FBS was used.

TABLE 3

The result of Culture at Day 6

| | Experiment No. | | | | |
|---|---|---|---|---|---|
| | 1 | 2 | 3 | 4 | 5 |
| Grown Cell Density (cell/cm²) | $4.0 \times 10^5$ | $5.7 \times 10^5$ | $4.4 \times 10^5$ | $2.5 \times 10^5$ | $3.2 \times 10^5$ |
| Total Cell Number | $1.8 \times 10^7$ | $2.6 \times 10^7$ | $3.9 \times 10^7$ | $3.4 \times 10^7$ | $2.9 \times 10^7$ |
| Amount of Produced Antibody Per Day mg/L/day | 3.8 | 4.6 | 12.0 | 8.3 | 7.4 |

TABLE 4

| | The result of Culture on Day 8 | | | | |
|---|---|---|---|---|---|
| | Experiment No. | | | | |
| | 1 | 2 | 3 | 4 | 5 |
| Growing Cell Density (cell/cm$^2$) | $4.8 \times 10^5$ | $6.0 \times 10^5$ | $3.9 \times 10^5$ | $3.4 \times 10^5$ | $2.9 \times 10^5$ |
| Total Cell Number | $2.2 \times 10^7$ | $2.7 \times 10^7$ | $4.0 \times 10^7$ | $3.5 \times 10^7$ | $2.4 \times 10^7$ |
| Amount of Produced Antibody Per Day mg/L/day | 6.1 | 6.5 | 14.2 | 15.5 | 12.2 |

Thereafter, an amount of a medium was changed from 20 mL to 40 mL on Day 9 of culture, and culture in each of experiments 1 to 5 was continued for 19 days in total. On Day 19, the culture bag was broken down, each module was accumulated in a bag, 40 mL of a medium was added thereto, and shaking culture was performed in a CO$_2$ incubator. Since a decrease in pH of the medium was observed within about one hour (FIG. 5), 0.5 mole of sodium hydroxide and 45% glucose were added once an hour and culture were performed for 6 hours. After performing culture, culture solutions were collected, cell count was determined by colorimetric quantification with CCK8, and an amount of antibody produced was determined by HPLC method. The cell density was $4.7 \times 10^5$ cells per square centimeter, the total cell number was $1.9 \times 10^8$, and the antibody production amount converted per day was 55 mg/L/day.

Example 2

Cell Culture Method Using Porous Polyimide Film with Siphon-Type Culture Device

Conditioned/suspended anti-human IL-8 antibody producing CHO-DP12 cells (ATCC CRL-12445) were suspension-cultured using a medium (BalanCD (Trademark) CHO GROWTH A) and culture was continued until viable cell count per mL was $3.9 \times 10^6$. After the suspension culture medium (12 mL each) was poured onto one dish (diameter, 10 cm), 12 modules were added to the dish, the module having a casing formed with a nylon mesh (30 #, mesh opening 547 μm) and having a fixed amount (20 cm$^2$ per module) of porous polyimide film aseptically added and sealed therein. The module was wetted with the cell suspension and then left overnight in a CO$_2$ incubator.

On the next day, the module was taken out and 10 modules were placed on the stage part of the siphon type cell culture device depicted in FIG. 9, 350 mL of medium (IMDM containing 2% FBS) was pooled in a sump, and the medium was circulated via a tube pump at a rate of 60 mL/min. After 2 days, culture was terminated. Cells at a cell density of $5.5 \times 10^4$ cells/cm$^2$ with a total cell count of $1.2 \times 10^7$ were observed.

Example 3

Cell Culture Method Using Porous Polyimide Film with Siphon-Type Culture Device

Conditioned/suspended anti-human IL-8 antibody producing CHO-DP12 cells (ATCC CRL-12445) were suspension-cultured using a medium (BalanCD (Trademark) CHO GROWTH A) and culture was continued until viable cell count per mL was $9.9 \times 10^6$. Ten modules were placed in an oxygen permeable bag for shaking culture, and shaking culture was performed overnight in a CO$_2$ incubator.

On the next day, the module was taken out from the shaking bag and subjected to cell culture with a siphon type culture device under the same conditions as in Example 2. 350 mL of medium (KBM270 manufactured by Kohjin Bio Co., Ltd.) was pooled in a sump, and the medium was circulated via a tube pump at a rate of 60 mL/min. When culture was terminated after 4 days, cells at a cell density of $1.0 \times 10^5$ cells/cm$^2$ with a total cell count of $2.1 \times 10^7$ were observed.

Example 4

Cell Culture Method Using Porous Polyimide Film with Cylindrical Vapor Phase Culture Device Conditioned/suspended anti-human IL-8 antibody producing CHO-DP12 cells (ATCC CRL-12445) were suspension-cultured using a medium (BalanCD (Trademark) CHO GROWTH A) and culture was continued until viable cell count per mL was $9.9 \times 10^6$. Ten modules were placed in an oxygen permeable bag for shaking culture, and shaking culture was performed overnight in a CO$_2$ incubator.

On the next day, the module was taken out and 10 modules were placed on the stage part of the cylindrical vapor phase cell culture device depicted in FIG. 10, 350 mL of medium (KBM270 manufactured by Kohjin Bio Co., Ltd.) was pooled in a sump, and the medium was circulated via a tube pump at a rate of 20 mL/min. When culture was terminated after 4 days, cells at a cell density of $2.5 \times 10^5$ cells/cm$^2$ with a total cell count of $5.0 \times 10^7$ were observed. The fact was demonstrated that a large amount of antibody-producing cells can be cultured with a compact and simple facility without using an oxygen supply device.

Example 5

Cell Culture Method Using Porous Polyimide Film with Cylindrical Vapor Phase Culture Device Conditioned/suspended anti-human IL-8 antibody producing CHO-DP12 cells (ATCC CRL-12445) were suspension-cultured using a medium (BalanCD (Trademark) CHO GROWTH A) and culture was continued until viable cell count per mL was $2.4 \times 10^6$. 30 modules were sealed in an oxygen-permeable culture bag, the module having a mantle (casing) formed with a nylon mesh (30 #, mesh opening 547 μm) and having a fixed amount (20 cm$^2$ per module) of porous polyimide film aseptically added and sealed therein, and then 30 mL of the medium mentioned above was poured therein. On the next day, after left in a CO$_2$ incubator overnight, the module was taken out and 30 modules were placed on the stage part of the cylindrical vapor phase cell culture device depicted in FIG. 11, 300 mL of medium (KBM270 manufactured by Kohjin Bio Co., Ltd.) was pooled in a sump, and the medium was circulated via a tube pump at a rate of 20 mL/min.

When culture was terminated after 4 days, cells at a cell density of $7.1 \times 10^4$ cells/cm$^2$ with a total cell count of $5.8 \times 10^7$ were observed. The fact was demonstrated that a large amount of antibody-producing cells can be cultured with a compact and simple facility without using an oxygen supply device.

Example 6

Cell Culture Method with Mist and Shower Type Culture Device Using Porous Polyimide Film Conditioned/suspended anti-human IL-8 antibody producing CHO-DP12 cells (ATCC CRL-12445) were suspension-cultured using a medium (BalanCD (Trademark) CHO GROWTH A) and culture was continued until viable cell count per mL was $3.9 \times 10^6$. After the suspension culture medium (12 mL each) was poured onto one dish (diameter, 10 cm), 12 modules were added to the dish, the modules having a casing formed with a nylon mesh (30 #, mesh opening 547 μm) and having a fixed amount (20 cm² per module) of porous polyimide film aseptically added and sealed therein. The module was wetted with the cell suspension and then left overnight in a $CO_2$ incubator.

On the next day, the module was taken out and 12 modules were placed on the stage part of the mist and shower type cell culture device depicted in FIG. 12, 200 mL of medium (IMDM containing 2% FBS) was pooled in a sump, and the medium was circulated via a tube pump at a rate of 60 mL/min.

When culture was terminated after 2 days, cells at a cell density of $3.4 \times 10^4$ cells/cm² with a total cell count of $8.2 \times 10^6$ were observed.

Example 7

Cell Culture Method with Mist and Shower Type Culture Device Using Porous Polyimide Film Conditioned/suspended anti-human IL-8 antibody producing CHO-DP12 cells (ATCC CRL-12445) were suspension-cultured using a medium (BalanCD (Trademark) CHO GROWTH A) and culture was continued until viable cell count per mL was $9.9 \times 10^6$. Ten modules were placed in an oxygen permeable bag for shaking culture, and shaking culture was performed overnight in a $CO_2$ incubator.

On the next day, the module was taken out from the shaking bag and subjected to cell culture with a mist and shower type culture device under the same conditions as in Example 7. 200 mL of medium (KBM270 manufactured by Kohjin Bio Co., Ltd.) was pooled in a sump, and the medium was circulated via a tube pump at a rate of 60 mL/min. When culture was terminated after 4 days, cells at a cell density of $8.8 \times 10^4$ cells/cm² with a total cell count of $1.8 \times 10^7$ were observed.

Example 8

Vapor Phase Exposed Type Rotating Cell Culture Device

Conditioned/suspended anti-human IL-8 antibody producing CHO-DP12 cells (ATCC CRL-12445) were suspension-cultured using a medium (BalanCD (Trademark) CHO GROWTH A) and culture was continued until viable cell count per mL was $1.3 \times 10^6$. In a vapor phase exposed type rotating cell culture device (vertical drum type, without spiral flow channel) depicted in FIG. 13, 18 modules were placed, the module having a mantle (casing) formed with a nylon mesh (30 #, mesh opening 547 μm) and having a fixed amount (20 cm² per module) of porous polyimide film aseptically added and sealed therein, and prepared ready-for-rotation. After 40 mL of the suspension culture medium was added to the upper sump, and the rotating part was wetted with the suspension culture medium at a slow speed as low as 6 rpm. After leaving the entire device including this rotating part in a $CO_2$ incubator for 5 hours, the suspension culture medium in the upper sump was removed and 500 mL of medium (IMDM containing 2% FBS) was added from the lower sump in which the medium was pooled, while continuing the rotation of the module, and the medium was circulated via a tube pump at a rate of 10 mL/min. When culture was performed for 7 days, cells at a cell density of $3.2 \times 10^5$ cells/cm² with a total cell count of $1.0 \times 10^8$ were observed.

Example 9

Vapor Phase Exposed Type Rotating Cell Culture Device

Conditioned/suspended anti-human IL-8 antibody producing CHO-DP12 cells (ATCC CRL-12445) were suspension-cultured using a medium (BalanCD (Trademark) CHO GROWTH A) and culture was continued until viable cell count per mL was $1.3 \times 10^6$. In a vapor phase rotating cell culture device (notched drum type, with spiral flow channel) depicted in FIG. 14, 18 modules were placed, the module having a casing formed with a nylon mesh (30 #, mesh opening 547 μm) and having a fixed amount (20 cm² per module) of porous polyimide film aseptically added and sealed therein, and prepared ready-for-rotation. After 40 mL of the suspension culture medium was added to the upper sump, and the rotating part was wetted with the suspension culture medium at a slow speed as low as 6 rpm. After leaving the entire device including this rotating part in a $CO_2$ incubator overnight, the suspension culture medium in the upper sump was removed and 500 mL of medium (IMDM containing 2% FBS) was added from the lower sump in which the medium was pooled, while continuing the rotation of the module, and the medium was circulated via a tube pump at a rate of 10 mL/min. When culture was performed for 7 days, cells at a cell density of $2.4 \times 10^5$ cells/cm² with a total cell count of $8.5 \times 10^7$ were observed.

Example 10

Culture of CHO-DP12 Cells in Bag Using Various Module

Conditioned/suspended anti-human IL-8 antibody producing CHO-DP12 cells (ATCC CRL-12445) were suspension-cultured using a medium (BalanCD (Trademark) CHO GROWTH A) and culture was continued until viable cell count per mL was $1.1 \times 10^6$. Six types of modules (FIG. 15; photograph of modules) including a module having a casing formed with a nylon mesh (30 #, mesh opening 547 μm) and a fixed amount (20 cm² per module) of porous polyimide film aseptically added and sealed therein, and a module in which a part of a porous polyimide film is fixed and exposed, were prepared. The 25 μm porous polyimide film in a various combination illustrated in Table 1 was placed aseptically in an oxygen-permeable culture bag, and the opening was welded to prepare a module-containing type culture bag. The configuration of each experiment is depicted in FIG. 15.

Into these culture bags, 6 mL of the cell suspension was poured, and after 2 hours and 5.5 hours, the number of unadsorbed and suspended cells was measured. It was found that number of unadsorbed cells were observed in response to the shape of modules and the shape of the porous polyimide film. The results are illustrated in Table 5.

TABLE 5

| | Experiment No. | | | | | |
|---|---|---|---|---|---|---|
| | 1 | 2 | 3 | 4 | 5 | 6 |
| After 2 hours Number of unadsorbed cells (cells/ml) | $7.8 \times 10^5$ | $7.0 \times 10^5$ | $2.4 \times 10^5$ | $1.4 \times 10^5$ | $3.9 \times 10^5$ | $2.5 \times 10^5$ |
| After 5.5 hours Number of unadsorbed cells (cells/ml) | $5.0 \times 10^5$ | $2.7 \times 10^5$ | $6.0 \times 10^4$ | $4.0 \times 10^4$ | $2.6 \times 10^5$ | $1.6 \times 10^5$ |

After the adsorption step was completed, 20 mL of the medium was supplied, and then shaking culture was performed in a $CO_2$ incubator. Medium was exchanged about twice a week while adding sodium hydroxide solution and a feed medium every day. When medium was exchanged, the cell count was measured by colorimetric method with CCK8 to confirm cell proliferation. Depending on the shape of the module, it was found that the proliferation behavior of the cell changed greatly. The cell counts on Day 4, Day 7 and Day 11 are summarized in Table 6.

TABLE 6

| | Experiment No. | | | | | |
|---|---|---|---|---|---|---|
| | 1 | 2 | 3 | 4 | 5 | 6 |
| After 4 days Growing Cell Density (cells/cm$^2$) | $2.8 \times 10^4$ | $4.3 \times 10^4$ | $3.1 \times 10^4$ | $5.8 \times 10^4$ | $8.8 \times 10^3$ | $1.0 \times 10^4$ |
| After 7 days Growing Cell Density (cells/cm$^2$) | $9.3 \times 10^4$ | $1.1 \times 10^5$ | $1.2 \times 10^5$ | $1.9 \times 10^5$ | $7.4 \times 10^3$ | $6.2 \times 10^3$ |
| After 11 days Growing Cell Density (cells/cm$^2$) | $1.2 \times 10^5$ | $1.2 \times 10^5$ | $1.2 \times 10^5$ | $2.4 \times 10^5$ | Not Measured | Not Measured |

Example 11

Novel Medium-Replacing Type Culture Method

Conditioned/suspended anti-human IL-8 antibody producing CHO-DP12 cells (ATCC CRL-12445) were suspension-cultured using a medium (BalanCD (Trademark) CHO GROWTH A) and culture was continued until cell count per mL was $2.0 \times 10^6$. Strips of the polyimide porous film having an elongated shape (0.3 cm×2.5 cm) were prepared and subjected to dry heat sterilization, then 11 to 12 strips were placed in a 20 cm$^2$ dish, 4 mL of the suspension culture medium was poured thereto, and after the porous polyimide film was thoroughly wetted with the cell suspension, it was left in a $CO_2$ incubator. After 2 hours, the dish was removed from the incubator, and after the cell suspension was aspirated and removed, 4 mL of a medium (IMDM with 2% FBS added thereto) was added and culture was continued in a $CO_2$ incubator. The medium was exchanged once every 2 days.

Seven days after the initiation of culture, the cell count on the porous polyimide film in three dishes cultured with CCK 8 was calculated as the cell count per area. On the next day, while in one of the three dishes culture was continued, in one of the remaining two dishes, the porous polyimide film on which the cells grew was transferred into an oxygen permeable culture bag manufactured by NIPRO CORPORATION along with the culture solution, and sealed aseptically with a heat sealer. With respect to the remaining dish, the porous polyimide film was aseptically cut into about 0.3 cm×0.3 cm strips with scissors, and then an outer bag made of 30 # nylon mesh was prepared and a bag having a size of about 1 cm×1 cm was aseptically formed with a heat sealer and the medium was transferred together with the outer bag to the oxygen permeable culture bag manufactured by NIPRO CORPORATION, and aseptically sealed with a heat sealer.

Stationary culture was continued as before, while a culture bag in which the porous polyimide film was directly placed and a culture bag in which the porous polyimide film having a mantle made from a nylon mesh was placed, were subjected to shaking culture for 2 days in shakers respectively placed in a $CO_2$ incubator set to cause 20 to 30 vibration per minute. Cell densities after stationary culture and two types of shaking culture were calculated by the same CCK 8 method as before culture. The results are illustrated in Table 7. Only in the case of shaking culture directly placed in a bag, a significant decrease in cell count was observed.

Figure 16:
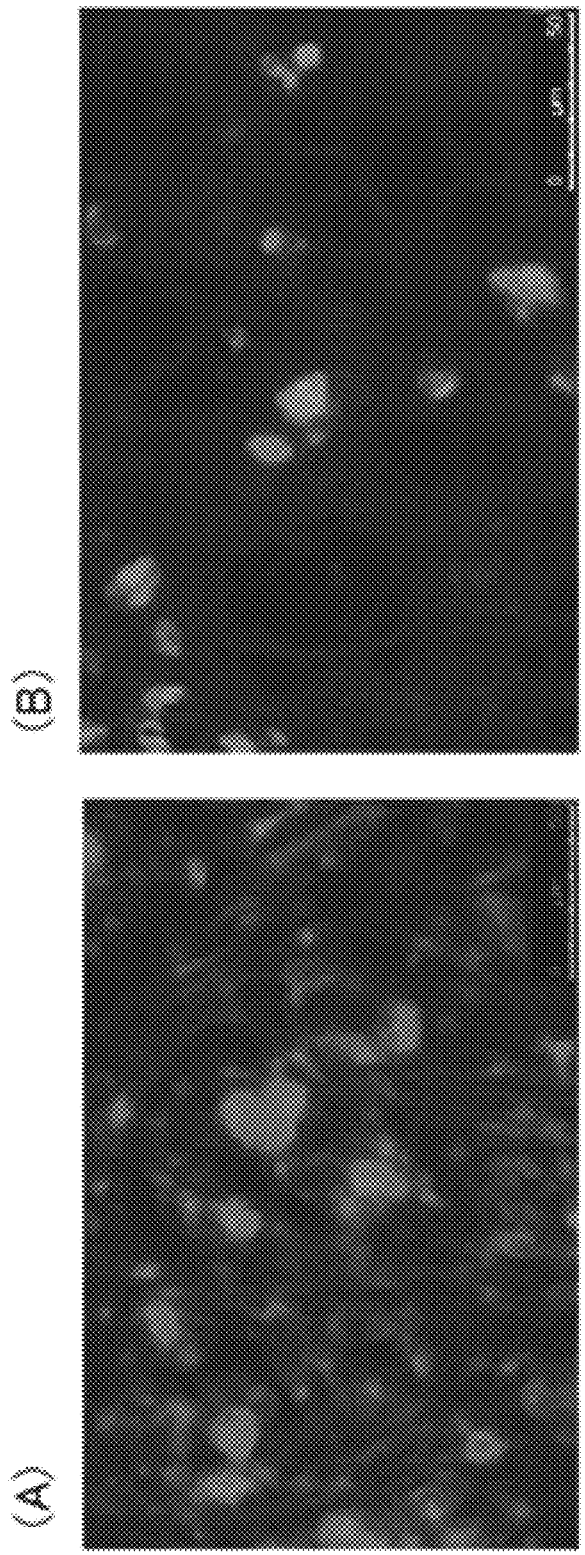
FIG. 16 represents a fluorescent microscope image of the porous polyimide film used in Example 12. A fluorescent microscope of CHO-DP12 cells after the cells were seeded and cultured for 2 days is illustrated. (A) After two days of stationary culture, (B) After two days of shaking culture (without a mesh).

The porous polyimide film was taken out from the bag in which the porous polyimide film had been directly placed, 1 mL of the medium was added, and CellMask Orange Plasma Membrane Stain (1 µL) and Hoechst 33342 (manufactured by PromoKine) (1 µL) were further added, and the resultant was stood still in an incubator for 5 minutes. Thereafter, the medium containing the staining reagent was removed and a fresh medium was added to complete the dyeing. Live cell imaging was performed with a fluorescence microscope. Similarly, the porous polyimide film was continued to be stationary cultured, and also subjected to imaging measurement under the same conditions. A large amount of cells are observed in stationary culture (FIG. 16 (A)). On the other hand, in the porous polyimide film directly placed in the shaking bag, only a very small amount of cells were visually recognized (FIG. 16 (B)). A fluorescence micrograph is depicted in FIG. 16.

TABLE 7

Change in Density of Cells Grown on Porous Polyimide Film

|  | Stationary Culture Cells/cm$^2$ | Shaking Culture: Directly Cells/cm$^2$ | Shaking Culture: in Mesh Cells/cm$^2$ |
|---|---|---|---|
| Before Culture | 6.6 × 10$^5$ | 6.6 × 10$^5$ | 6.9 × 10$^5$ |
| After Culture | 7.0 × 10$^5$ | 1.2 × 10$^4$ | 6.6 × 10$^5$ |
| After Culture/ Before Culture | 1.06 | 0.02 | 0.72 |

Example 12

Figure 17:
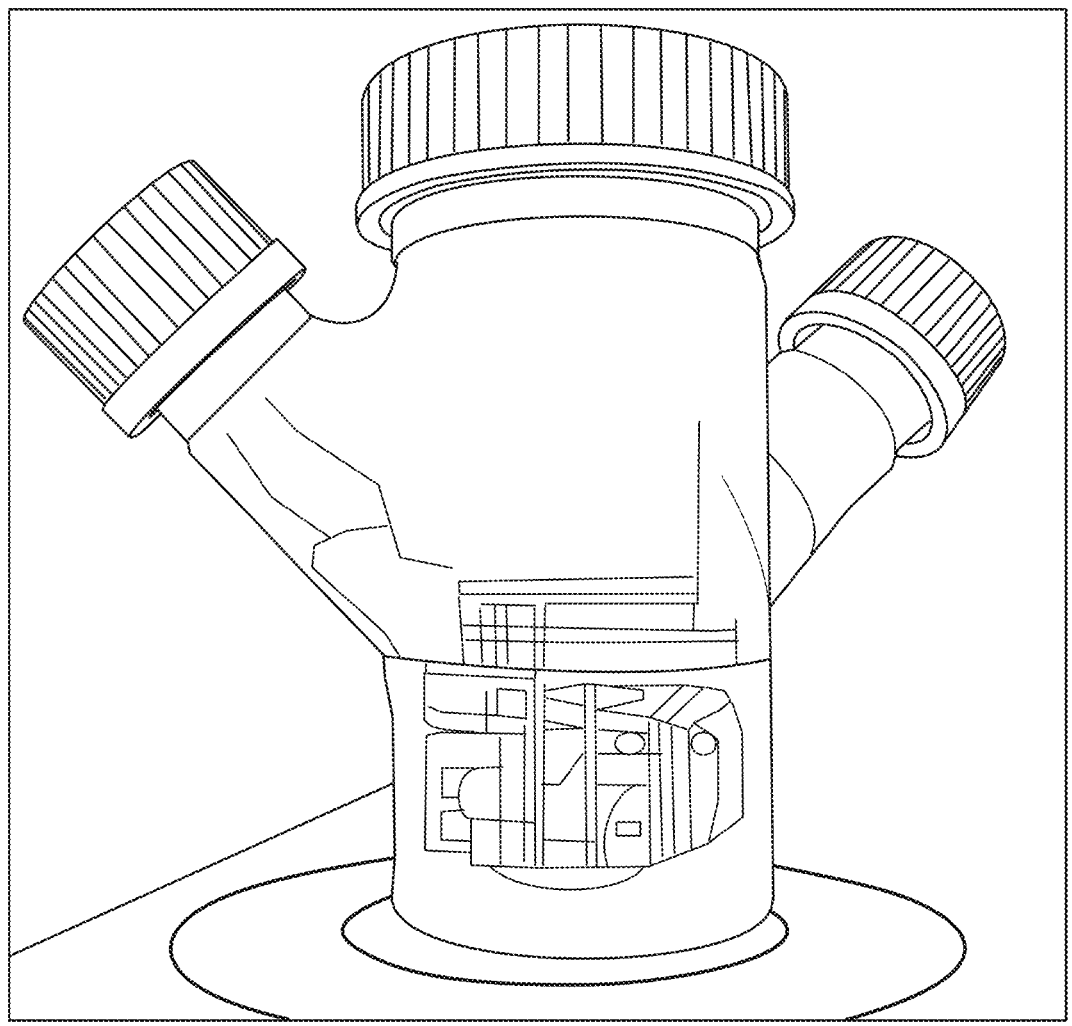
FIG. 17 represents an embodiment of a cell culture performed in Example 13.

Method for Cell Culture of Human Mesenchymal Stem Cells Using Module Containing Porous Polyimide Film Human mesenchymal stem cells manufactured by Lonza Group AG were subcultured and grown in a dish and 5.0×10$^6$ cells were suspended in 20 mL of medium by trypsinization. In an oxygen permeable culture bag, 30 modules having a mantle (casing) formed with a nylon mesh (30 #, mesh opening 547 μm) and having a fixed amount (20 cm$^2$ per module) of a porous polyimide film aseptically added and sealed, were placed, to which was added the suspension, and the shaking culture was performed overnight in a CO$_2$ incubator. On the next day, after discarding the liquid in the bag, the bag was aseptically transferred to a vessel (FIG. 4 (A)) that was a spinner flask to which a module retention function had been imparted, 80 mL of a dedicated medium for mesenchymal stem cell and agitating culture was performed in a CO$_2$ incubator (FIG. 17). After 1 week of stirring culture, the cell count was determined by colorimetric method using CCK8, 5.5×10$^7$ cells were confirmed. It was demonstrated that a large amount of human mesenchymal stem cells can be easily cultured by the spinner culture method.

Example 13

Method for Substance Production Using a Module Containing a Porous Polyimide Film and WAVE Type Bioreactor Conditioned/suspended anti-human IL-8 antibody producing CHO-DP12 cells (ATCC CRL-12445) were suspension-cultured using a medium (BalanCD (Trademark) CHO GROWTH A) and culture was continued until viable cell count per mL was 2.1×10$^6$.

Three hundred modules were prepared by forming casing with an intersection-fused polypropylene mesh (25 #, mesh opening 670 μm) manufactured by Clever, Co., Ltd., adding a fixed amount (10 cm$^2$ per module) of a porous polyimide film and two liners made of intersection-fused polypropylene mesh (10 #, mesh opening 2,145 μm) to the casing, and sealing the resultant. The module was aseptically introduced through a cap attached to a bag for ReadyToProcess WAVE 25 (bioreactor manufactured by GE Healthcare; hereinafter referred to as WAVE 25). The bag was placed in WAVE 25, and air, CO$_2$ concentration, temperature, etc. were set to complete preparation. The suspension culture medium (500 mL) was aseptically added to the bag through a tube, and vibration was started at 37° C., 5% CO$_2$ concentration to perform cell adsorption to the porous polyimide film. FIG. 18 represents a bag containing a reactor and a module. After 24 hours, the medium which had been poured was discharged from the bag, and 500 mL of CHO medium KBM 270 manufactured by Kohjin Bio Co., Ltd. was added thereto. When the liquid discharged from the bag was subjected to cell count, the viable cells count per mL was 1.1×10$^6$. 48% of viable cells are calculated to be adsorbed.

Figure 19:
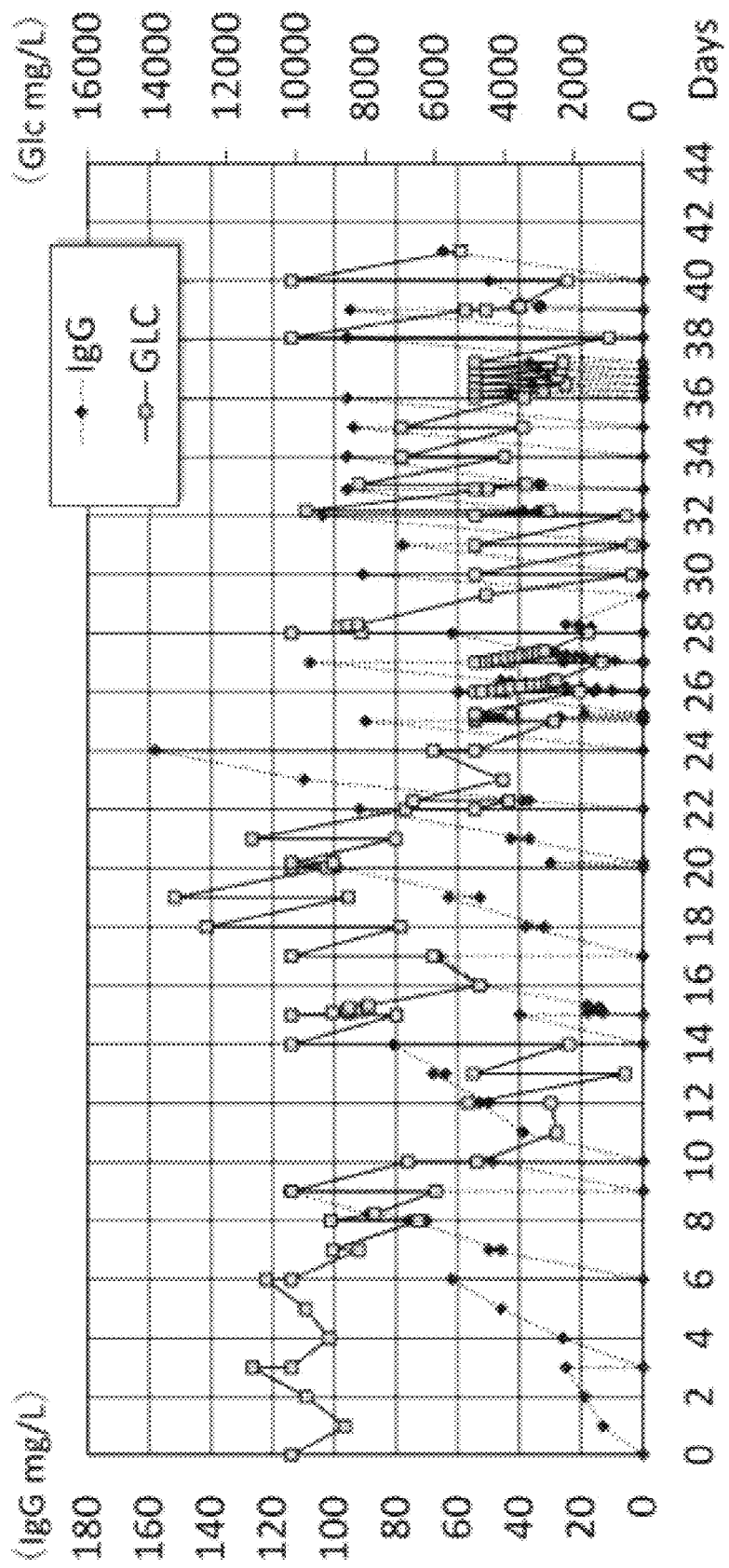
FIG. 19 is a graph illustrating changes with time in an amount of antibody and a concentration of glucose produced from anti-human IL-8 antibody producing CHO-DP12 cells which is cultured by applying the present invention in an embodiment.

In order to analyze the change in the condition in the bag, the medium was periodically sampled and analyzed for compositions of various components such as a glucose level, an amount of lactic acid production, an amount of antibody production, etc. using Cedex Bio manufactured by Roche. The medium was exchanged intermittently once every 1 to 2 days and cell culture was continuously performed for about 40 days. In the latter half of the experiment, as illustrated in FIG. 19, medium exchange was conducted several times a day, and the effects and the like were verified. FIG. 19 illustrates the time course of the amount of antibody production and glucose concentration. The consumption of glucose and the amount of antibody production were illustrated to be gradually increased and the fact that antibodies can be produced continuously with highly efficiency was found. Antibody production efficiency per day throughout the whole culture period was 64 mg/L.

Example 14

<Fabrication of Modularized Porous Polymer Film Having a Stainless Steel Casing (Hereinafter Referred to as "Metal Module") and a Stainless Steel Cell Culture Unit (Hereinafter Referred to as "Metal Drum")>

In order to fully utilize the heat resistance of the porous polyimide film and complete the sterilization operation by a simple bulk dry heat sterilization, a metal module composed of a stainless steel mesh casing, a liner, and a porous polyimide film was prepared (see, FIG. 20 (A)). Specifically, a laminate of a 1 cm×1 cm porous polyimide film and a porous polyimide film laminated with a stainless steel mesh (referred to as "liner", not illustrated) having the same area (3 porous polyimide films, 1 liner, 4 porous polyimide films, 1 liner, 3 porous polyimide films, stacked in this order) were sealed in a stainless steel mesh casing to prepare a metal module (FIG. 20 (A)). The operation was performed in a non-sterilized fashion in an open space. A metal drum for operating this metal module was similarly fabricated with a stainless steel mesh (FIG. 20 (B)), and assembled in a non-sterile manner so as to contain 20 metal modules inside. After that, the metal drum containing the metal modules was wrapped with aluminum foil, dry heat sterilized at 190° C. for 80 minutes, and allowed to cool.

<Vapor Phase Exposed Type Rotating Cell Culture Device>

Conditioned/suspended anti-human IL-8 antibody producing CHO-DP12 cells (ATCC CRL-12445) were suspension-cultured using a medium (BalanCD (Trademark) CHO GROWTH A) and culture was continued until viable cell count per mL was 1.1×10$^6$. As depicted in FIG. 20 (C), a metal drum including a metal module was aseptically placed and prepared ready-for-rotation in a clean environment (FIG. 20 (C)). After 34 mL of the medium obtained by suspension culture of the cells as described above and 6 mL of fresh medium (BalanCD (trademark) CHO GROWTH A) were poured into a culture tank (corresponding to the culture tank in FIG. 13 (A)), the metal drum was rotated at a rate of 1 rpm to wet the porous polyimide film with the medium.

After leaving the whole device in a CO$_2$ incubator for 21 hours, the medium in the upper sump was removed, and while the rotation of the metal drum was continued, the medium was circulated via a tube pump at a rate of 10 mL/min from a medium discharge tank (corresponding to the medium discharge tank in FIG. 13 (A)) in which 200 mL of the medium (KBM-270) was pooled. When culture was performed for 4 days, cells at a cell density of 3.9×10$^5$ cells/cm$^2$ with a total cell count of 7.8×10$^7$ were observed. After that, the total volume of the medium in the upper and lower sumps was exchanged with a fresh medium (KBM-270), and the culture was continued under the same conditions for another 2 days. At that time, cells at a cell density of 1.3×10$^6$ cells/cm$^2$ with a total cell count of 2.6×10$^8$ were observed.

Example 15

Preparation of a Cylindrical Gas Phase Culture Device (Hereinafter Referred to as "Vapor Cylinder Type Bioreactor") with a Modularized Porous Polymer Film (Hereinafter Referred to as "Metal Module") Having a Stainless Steel Casing and a Cell Culture Using it In order to fully utilize the heat resistance of the porous polyimide film and complete the sterilization operation by a simple bulk dry heat sterilization, a metal module composed of a stainless steel mesh casing, a liner, and a porous polyimide film was prepared (corresponding to FIG. 20 (A)). Specifically, a laminate of a 1 cm×1 cm porous polyimide film and a porous polyimide film laminated with a stainless steel mesh (referred to as "liner", not illustrated) having the same area (3 porous polyimide films, 1 liner, 4 porous polyimide films, 1 liner, 3 porous polyimide films, stacked in this order) were sealed in a stainless steel mesh casing to prepare a metal module (FIG. 20 (A)). The operation was performed in a non-sterilized fashion in an open space.

In the glass heat-resistant vapor cylinder type reactor for operating the metal module, a metal module is placed in the glass chamber, and the medium can be supplied into the vapor cylinder by dropping. Since a vapor cylinder type bioreactor equipped with a metal module is exclusively made of a heat resistant material, sterilization can be performed only using simple dry heat sterilization. After 30 metal modules were placed in a heat-resistant vapor cylinder, the device aseptically assembled was wrapped with aluminum foil, dry heat sterilized at 190° C. for 80 minutes, and allowed to cool to complete sterilization.

Using the prepared vapor cylinder type bioreactor, experiment for culturing human skin fibroblasts was started.

As described above, the entire vapor cylinder type reactor was assembled aseptically and the whole device was placed in a CO$_2$ incubator (FIG. 21). Human skin fibroblasts cultured on a dish were detached by trypsin treatment to prepare a cell suspension (70 mL, each) for the respective reaction mode depicted in FIGS. 22 (A) to (C). The cell density per mL at this point was 1.4×10$^5$. The cell proliferation behavior after adsorption is described in Table 8.

TABLE 8

| Medium Addition Mode | Liquid Supply (1) Drop-type (FIG. 22 (A)) | Liquid Supply (2) Mesh-type (FIG. 22 (B)) | Liquid Supply (3) Shower-type (FIG. 22 (C)) |
|---|---|---|---|
| Residual Cell Density in Liquid | Below Detection | 1.4 × 10$^4$ | Below Detection Limit |

TABLE 8-continued

Figure 22:
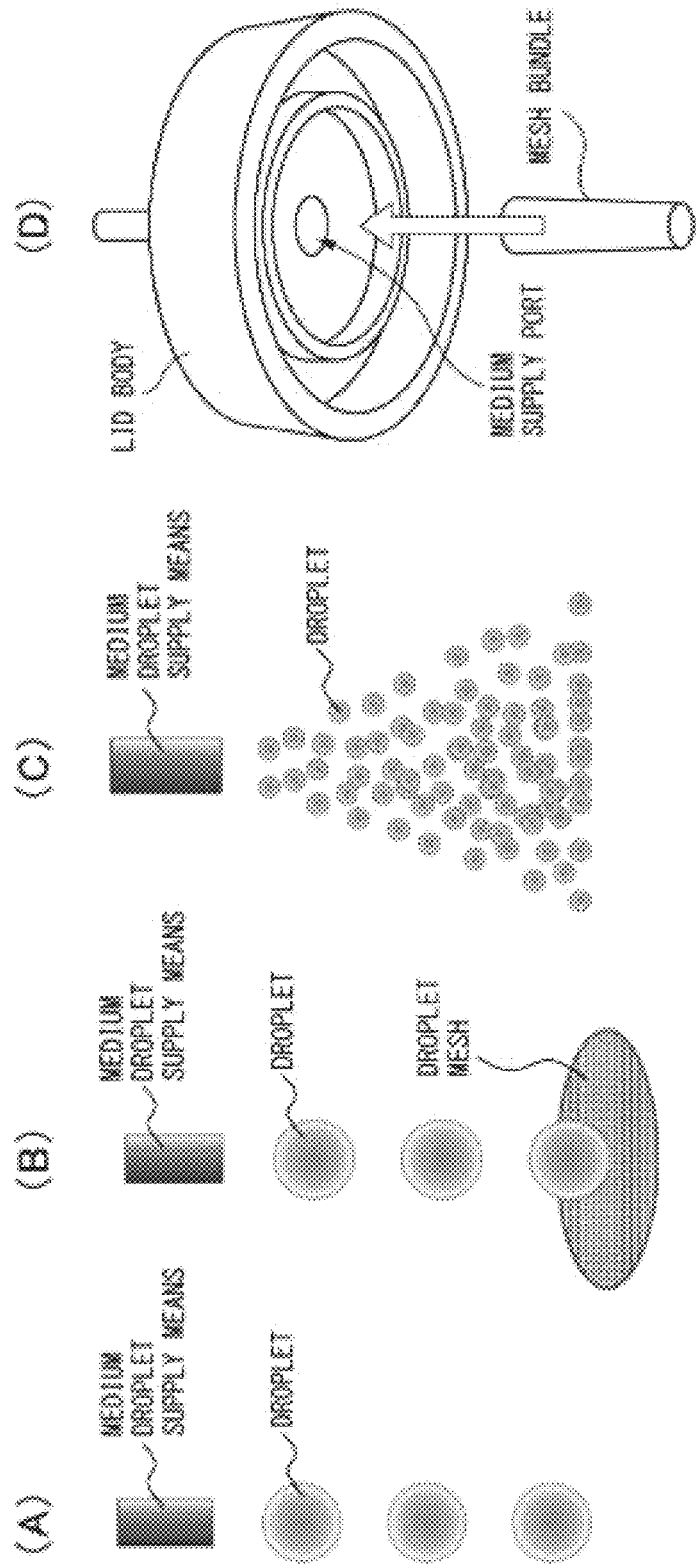
FIG. 22 is a conceptual diagram illustrating a mode of the medium added dropwise from a medium droplet supply means in the cell culture device according to one embodiment. (A) represents a drop-type device, (B) represents a mesh-type device, and (C) represents a shower type device. (D) is a diagram illustrating a lid body applied to a cell culture device according to an embodiment which is used to supply droplets in a drop-type and mesh-type device. A mesh bundle formed by rolling mesh made of stainless steel is inserted through a medium supply port of the lid body.

| Medium Addition Mode | Liquid Supply (1) Drop-type (FIG. 22 (A)) | Liquid Supply (2) Mesh-type (FIG. 22 (B)) | Liquid Supply (3) Shower-type (FIG. 22 (C)) |
|---|---|---|---|
| Cells/ml (*1) | Limit | | |
| Cell Adsorption (*2) | ~100% | 90% | ~100% |
| Expected Initial Maturity (Compared with Maximum Value) (*3) | 15% | 14% | 15% |
| Maturation on Day 5 (*4) | 12.8% (Upper) 10.2% (Lower) | 26.7% | 19.3% (Upper) 20.8% (Lower) |

(*1): The residual cell density in the liquid indicates the number of cells (density) remaining in the cell suspension after absorbing the cells to the porous polyimide film.
(*2): Cell adsorption ratio indicates how much cells in the cell suspension used for seeding have been adsorbed on the porous polyimide film.
(*3): Expected initial maturity is expressed as the number of adsorbed cells in actual cells as %, assuming that the maximum population of cells in the porous polyimide film is 100%.
(*4): The same as *3 (calculated on Day 5 of culture). Upper; the value of the top module, Lower; the value of the top module, respectively.

As depicted in FIG. 22 (D), a drop type droplet was attained by introducing a rolled-up stainless steel mesh (product number E 9103, 20 #, manufactured by Kyuho Corporation, Japan) (corresponding to a mesh bundle in FIG. 22 (D)) through a medium supply port provided in a lid body. In addition to the drop type method, droplet of a mesh type was attained by providing a planar stainless steel mesh (product number: E9103, 20 #, manufactured by Kyuho Corporation, Japan) directly under the mesh bundle to cover the module. Droplet of a shower type was attained by using a nozzle of product number 1/8 MVVP 6503 PP-IN manufactured by H.IKEUCHI Co., Ltd.

Thereafter, by continuously supplying a medium (using_KBM Fibro Assist manufactured by Kohjin Bio Co., Ltd.) using a pump, circulation of the medium was started and continuous culture was performed. Culture was continued while exchanging medium once every 3 days. Regarding the evaluation of the cell count, 1 to 2 modules were taken out of 30 modules, and cell count of human skin dermal fibroblasts growing in those modules was measured using the color reaction of CCK8. As is apparent from this experimental result, in this experiment, it was found that how to pour the medium solution determines the cell count in the module in each of the subsequent system. Interestingly, it was also observed that the effect of leveling of the liquid penetration by a mesh was very great, resulting in steady proliferation of cells. On the other hand, in the drop addition method, it was thought that the medium failed to spread throughout the inside of the reactor, and the cell growth region was limited due to the drift, which caused the decreased cell count. It is thought that the method of pouring the culture medium in a shower-like manner also contributes liquid leveling effect to some degree.

Figure 23:
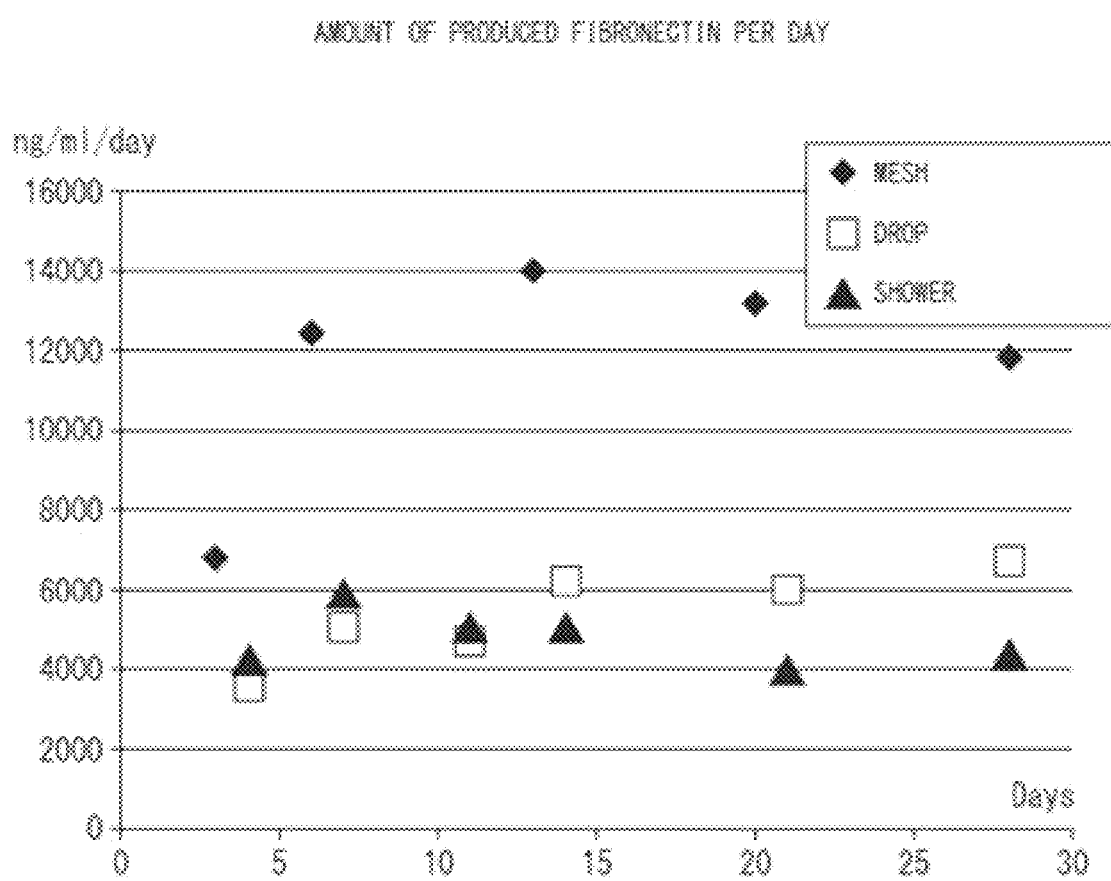
FIG. 23 is a graph illustrating an amount of fibronectin produced from human skin fibroblasts when the cell culture device of the present invention is used in one embodiment.

Subsequently, in order to verify efficiency of a bioreactor in the present culture method, we proceeded with evaluation of substance productivity. ELISA-kit for measuring human fibronectin manufactured by Takara Bio Inc. was used to measure the amount of the produced fibronectin. The measurement results are depicted in FIG. 23.

As is obvious from FIG. 11, a mesh culture method overwhelmingly predominates also in this substance production evaluation, and has been steadily increasing fibronectin productivity. Stable operation for 1 month could be attained. On the other hand, also in the shower type and drop type devices, stable substances were attained, but improvement in productivity could not be observed. It was possible to demonstrate that vapor phase exposed type culture enabled stable culture of human primary cells and high efficient production of valuable substances, using a very simple device.

Example 16

Metal Module and Heat-Resistant Siphon Reactor Made of Glass

In order to fully utilize the heat resistance of the porous polyimide film and complete the sterilization operation by a simple bulk dry heat sterilization, a metal module composed of a stainless steel mesh casing, a liner, and a porous polyimide film was prepared (FIG. 20 (A)). Specifically, a laminate of a 1 cm×1 cm porous polyimide film and a porous polyimide film laminated with a stainless steel mesh (referred to as "liner", not illustrated) having the same area (3 porous polyimide films, 1 liner, 4 porous polyimide films, 1 liner, 3 porous polyimide films, stacked in this order) were sealed in a stainless steel mesh casing to prepare a metal module (FIG. 20 (A)). The operation was performed in a non-sterilized fashion in an open space.

A glass heat-resistant siphon reactor for operating this metal module was designed based on a Soxhlet extractor and was prepared using only glass and metal in order to impart heat resistance (FIG. 24 (A)). A heat-resistant siphon reactor made of glass containing a metal module (FIG. 20(A)) is illustrated. A device was assembled by stacking 30 stainless steel modules inside this reactor in non-sterilized fashion. After that, the reactor part was wrapped with aluminum foil, dry heat sterilized at 190° C. for 80 minutes, and allowed to cool.

Figure 25:
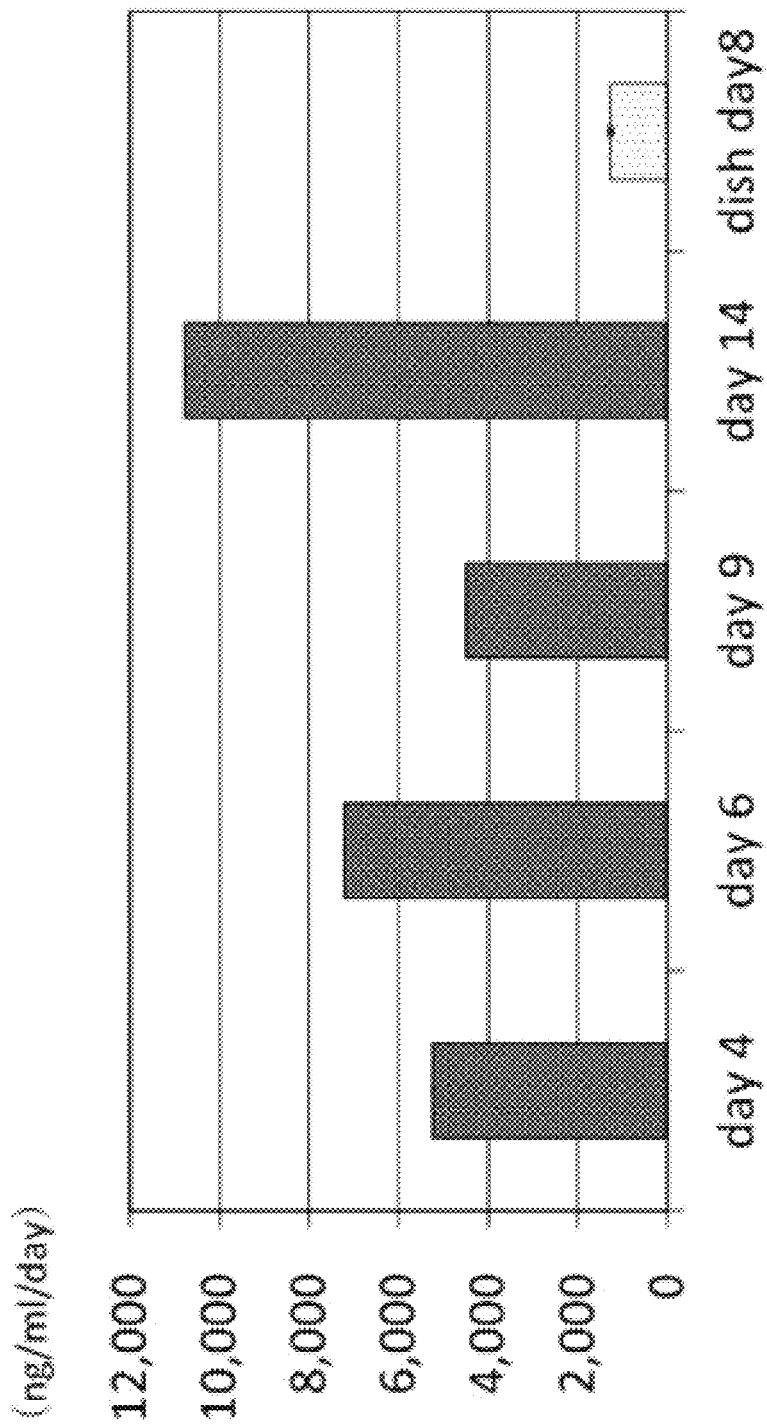
FIG. 25 is a graph illustrating an amount of fibronectin produced from human skin fibroblasts when the cell culture device of the present invention is used in one embodiment. As a control, the amount of fibronectin produced by culturing human skin fibroblasts in an ordinary culture dish is illustrated (dish day 8).

Next, liquid-phase/air-phase culture of human dermal fibroblasts was performed with a heat-resistant siphon reactor. As depicted in FIG. 24 (A), the entire reactor was assembled aseptically and the whole device was placed in a $CO_2$ incubator (FIG. 24 (B)). Human skin fibroblasts cultured in a dish were detached by trypsin treatment to prepare 70 mL of a cell suspension. Upon cell counting, the number of viable cells per mL was $1.4 \times 10^5$. 70 mL of the suspension was poured into a Soxhlet pipe having a metal module placed therein and allowed to stand for 30 minutes. After standing still, the internal liquid was drained off aseptically, and the drained liquid was poured again in the siphon reactor. This operation was repeated three times, then the liquid part was sampled and the cell count was measured to be $8.0 \times 10^3$. It can be mentioned that 94% of the cells were adsorbed by natural contact under such stationary conditions. Next, the siphon function was developed by continuously supplying a medium (using KBM Fibro Assist manufactured by Kohjin Bio Co., Ltd.) using a pump, whereby the medium and air (oxygen) were stably and circularly supplied inside the metal module. Culture was continued while exchanging medium once every 3 days. The fact that the stable and large amount of fibronectin was produced was determined with an ELISA-kit for measuring human fibronectin manufactured by Takara Bio Inc., and it was confirmed that highly efficient substance production was easily and continuously achieved (FIG. 25).

As depicted in the figure, since the substance production per day per unit volume is excellent and, unlike conventional culture in a dish, scale-up is very easy, and thus productivity may be improved with a compact device. Using a human primary cell as a basis for substance production, a continuous production system was prepared and a method of producing rare substances and valuable substances without using a complicated device having means such as oxygen supply was demonstrated.

Example 17

Method for Removing Animal Cells Utilizing Flexibility of Porous Polyimide Film

Figure 26:
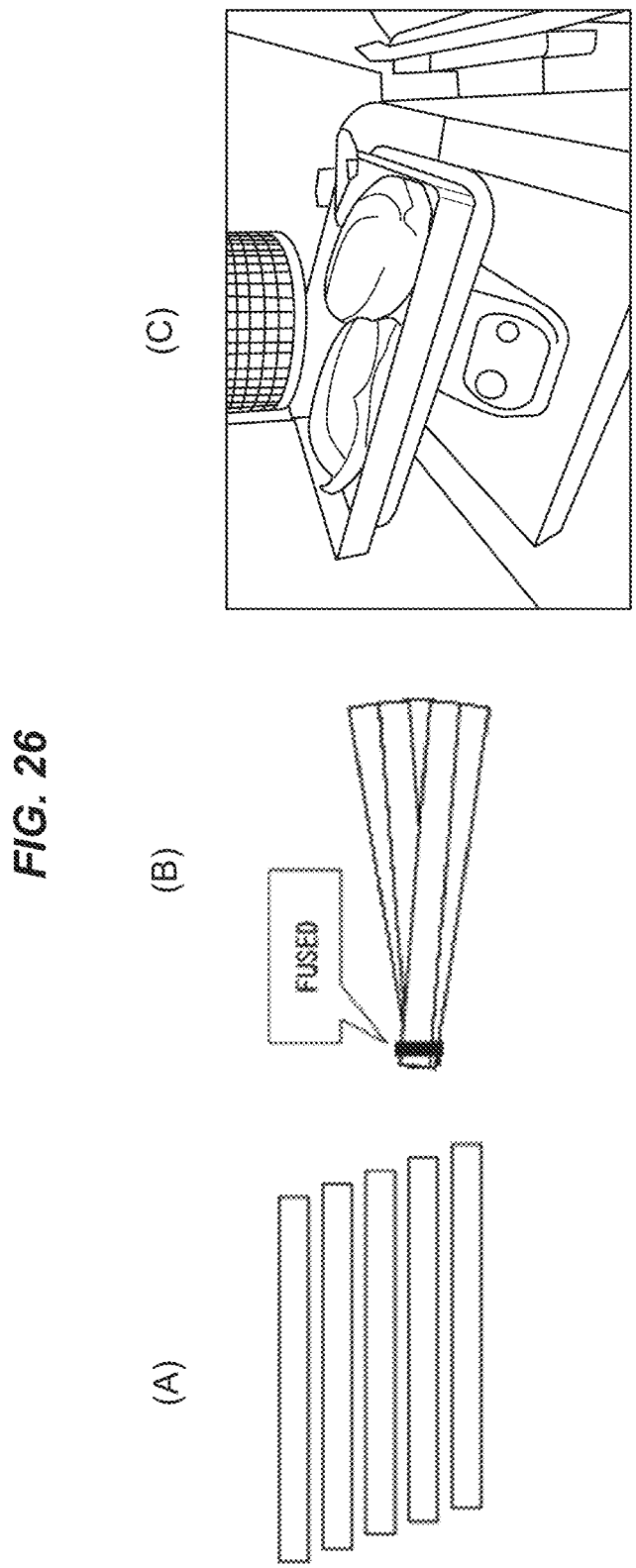
FIG. 26 illustrates a diagram representing a culture substrate (porous polyimide film) used in an embodiment of the invention and a cell culture device using it. (A) illustrates a strip-like porous polyimide film, and (B) illustrates a porous polyimide film one end of which is fused and fixed. (C) illustrates porous polyimide films (A) and (B) respectively sealed in a culture bag during shaking culture.

Conditioned/suspended anti-human IL-8 antibody producing CHO-DP12 cells (ATCC CRL-12445) were suspension-cultured using a medium (BalanCD (Trademark) CHO GROWTH A) and culture was continued until viable cell count per mL was $6.9 \times 10^5$. The culture substrate which was subsequently used is illustrated in Table 9 (FIGS. 26 (A) and (B)). In order to induce morphological change at high efficiency to efficiently induce cell death, a porous polyimide film having an elongated form was selected instead of a porous polyimide film having, for example, square form which was used in the ordinary culture.

TABLE 9

| Culture Substrate | Shape | Number · Area | Culture Bag |
|---|---|---|---|
| Method (1) Strip-like Fragment | Strip-like (5 cm × 0.5 cm) | 120 pieces · 300 cm² | Manufactured by Kohjin Bio Co., Ltd. |
| Method (2) Fixed Strip-Type | Every four strips of the rectangular strips described above were fused and fixed with polypropylene mesh | 30 bundles · 300 cm² | TAZETTA-F |

Under conditions illustrated in Table 9, the cell suspension (10 mL) was added to a culture bag in which a porous polyimide film with the same area and different shape was embedded, and stood still in an incubator (37° C., 5% $CO_2$) for 1 day to adsorb cells to the porous polyimide film (FIG. 26(C)). Subsequently, a suspension after cell adsorption was taken out of each bags, and a CHO cell culture medium (KBM270 manufactured by Kohjin Bio Co., Ltd., 20 mL each) was added, and stood still in the same incubator for 2 days. Cell growth behavior is illustrated in Table 10.

TABLE 10

| Culture Substrate | Maximum Cell Density and Cell Count When Medium is Replaced (Cells) (Cells/cm²) | After 2 Days of Culture Cell Count Cell Density | Growth Rate (Same as original value is taken as 100%) |
|---|---|---|---|
| Method (1) Strip-like Fragment | Total Cell Count $1.4 \times 10^7$ Maximum Cell Density $4.6 \times 10^4$ | $1.8 \times 10^7$ $5.9 \times 10^4$ | 128% |
| Method (2) Fixed Strip-Type | | $2.3 \times 10^7$ $7.7 \times 10^4$ | 167% |

Figure 27:
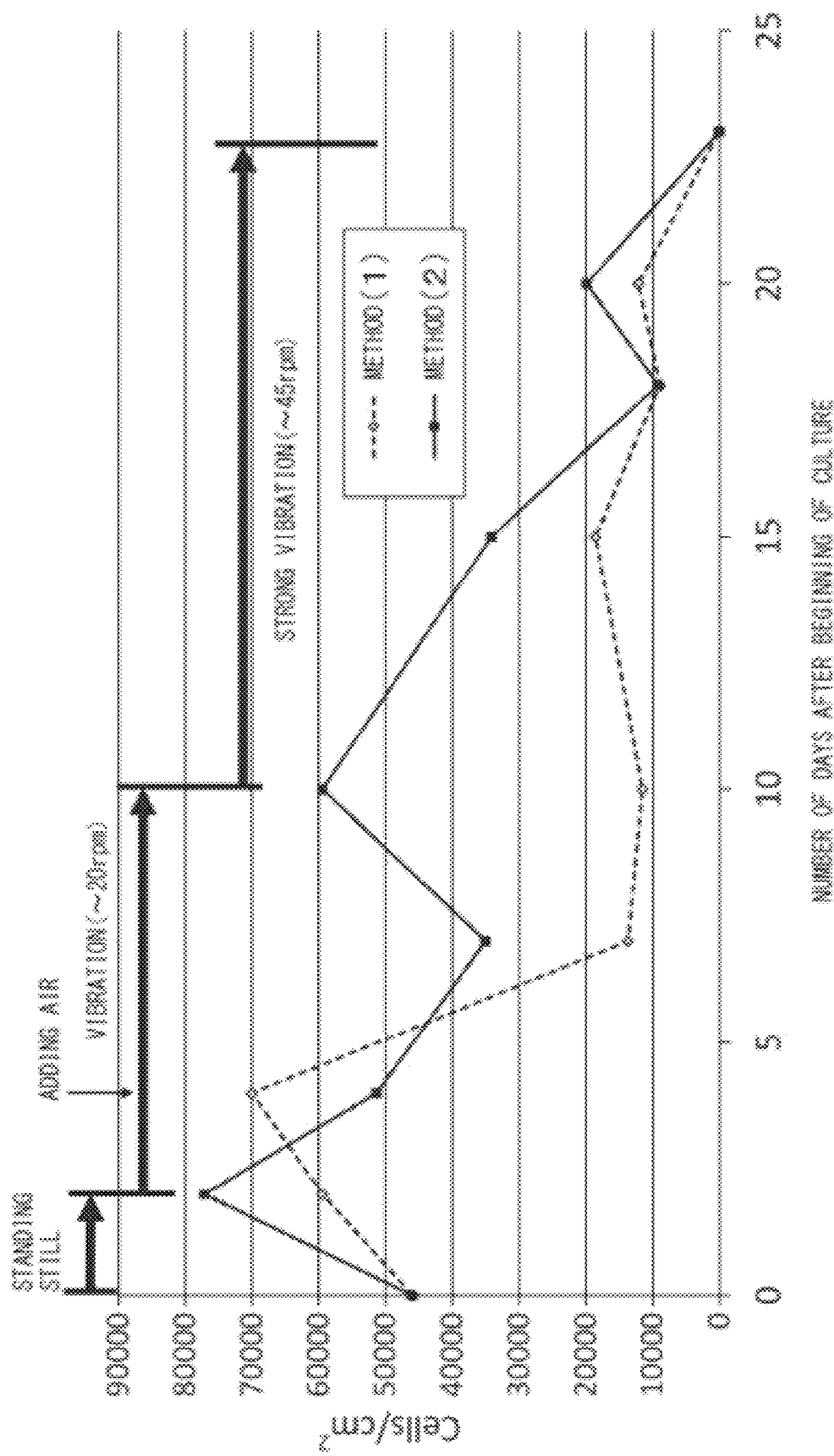
FIG. 27 illustrates a change in cell density of anti-human IL-8 antibody producing CHO-DP12 cells applied to a porous polyimide film of FIG. 26 (A): method (1) in Table 9, and FIG. 26 (B): method (2) in Table 9

As illustrated in Table 10, it was observed that the cells grew steadily in a culture bag containing the culture substrate depending on the properties of the respective culture substrate during stationary culture. Subsequently, a shaking mixer (SHM-2002) manufactured by LMS Co., Ltd. was placed in a $CO_2$ incubator, a culture bag was placed on the mixer, and shaking was begun (~20 rpm). After two days, in order to enhance the member deformation, 50 mL of air was added and the vibration was continued. Further, after ten days, the medium was increased to 50 mL to enhance shaking (~45 rpm). CCK8 was periodically used to measure the viable cell count. Change in cell count is depicted in FIG. 27. Unlike cell growth by stationary culture, decrease in cell count was induced depending on morphology of a culture substrate, and decrease in cell count proceeded with time. After 23 days, it was observed the fact that cells were killed. It was also found that the cell count was further decreased with change in shaking rate in method (2) (fixed strip type) wherein morphological change was partially suppressed. Depending on the shaking conditions and the shape of the culture substrate, a methodology for non-pharmaceutically killing animal cells has been established.

The invention claimed is:

1. A cell culture apparatus comprising:
    (a) a cell culture module;
    (b) a cell culture vessel, which is used for suspension culture; and
    (c) a cell culture device;
    wherein the cell culture module comprises:
        (I) a porous polymer film that is a porous polyimide film; and
        (II) a casing having two or more medium flow inlets, the casing containing the porous polymer film,
    wherein the porous polymer film is a three-layer structure porous polymer film having a surface layer A and a surface layer B, the surface layers having a plurality of pores, and a macrovoid layer sandwiched between the surface layers A and B;
    wherein an average pore diameter of the pores present in the surface layer A is smaller than an average pore diameter of the pores present in the surface layer B;
    wherein the macrovoid layer has partition walls bonded to the surface layers A and B, and a plurality of macrovoids surrounded by such partition walls and the surface layers A and B;
    wherein the pores in the surface layers A and B communicate with the macrovoid; and
    wherein the porous polymer film is contained within the casing with:
    two or more independent porous polymer films being stacked;
    wherein the porous polymer films are fixed in the casing, thereby preventing the porous polymer film from waving by fluid,
    wherein the cell culture module is used in a floating and a shaking or a stirring state in the cell culture vessel placed in the cell culture device,
    wherein the cell culture module is not fixed within the cell culture vessel, and
    wherein the casing comprises polyethylene, polypropylene, nylon, polyester, polystyrene, polycarbonate, polymethyl methacrylate, polyethylene terephthalate, stainless steel, or titanium.

2. The cell culture apparatus according to claim 1, wherein a diameter of the medium flow inlet is larger than a diameter of a cell, and smaller than a diameter at which the porous polymer films flow out.

3. The cell culture apparatus according to claim 1, wherein the casing has a mesh structure.

4. The cell culture apparatus according to claim 1, wherein the casing consists of an inflexible material.

5. The cell culture apparatus according to claim 1, wherein the porous polymer film has a plurality of pores having an average pore diameter of 0.01 to 100 μm.

6. The cell culture apparatus according to claim 1, wherein an average pore diameter of the surface layer A is 0.01 to 50 μm.

7. The cell culture apparatus according to claim 1, wherein an average pore diameter of the surface layer B is 20 to 100 μm.

8. The cell culture apparatus according to claim 1, wherein a total film thickness of the porous polymer film is 5 to 500 μm.

9. The cell culture apparatus according to claim 1, wherein the porous polyimide film comprises a polyimide derived from tetracarboxylic dianhydride and diamine.

10. The cell culture apparatus according to claim 1, wherein the porous polyimide film is a colored porous polyimide film that is obtained by molding a polyamic acid solution composition comprising a polyamic acid solution derived from tetracarboxylic dianhydride and diamine, and a coloring precursor, and subsequently heat-treating the resultant composition at 250° C. or higher.

11. The cell culture apparatus according to claim 1, wherein a liner is provided between the porous polymer films in the cell culture module.

* * * * *